US009642958B2

(12) United States Patent
Zilbershlag et al.

(10) Patent No.: US 9,642,958 B2
(45) Date of Patent: May 9, 2017

(54) COPLANAR WIRELESS ENERGY TRANSFER

(71) Applicant: Leviticus Cardio Ltd., Givat Shmuel (IL)

(72) Inventors: Michael Zilbershlag, Givat Shmuel (IL); Anton Plotkin, Tel-Aviv (IL)

(73) Assignee: Leviticus Cardio Ltd., Givat Shmuel (IL)

(*) Notice: Subject to any disclaimer, the term of this patent is extended or adjusted under 35 U.S.C. 154(b) by 445 days.

(21) Appl. No.: 14/041,698

(22) Filed: Sep. 30, 2013

(65) Prior Publication Data

US 2014/0031607 A1   Jan. 30, 2014

Related U.S. Application Data

(63) Continuation-in-part of application No. 13/588,524, filed on Aug. 17, 2012.

(60) Provisional application No. 61/525,272, filed on Aug. 19, 2011, provisional application No. 61/540,140, filed on Sep. 28, 2011, provisional application No. 61/708,333, filed on Oct. 1, 2012.

(51) Int. Cl.
| | |
|---|---|
| *H01F 38/00* | (2006.01) |
| *A61M 1/12* | (2006.01) |
| *A61N 1/378* | (2006.01) |
| *H01F 38/14* | (2006.01) |
| *A61N 1/372* | (2006.01) |

(52) U.S. Cl.
CPC ............ *A61M 1/127* (2013.01); *A61M 1/122* (2014.02); *A61N 1/3787* (2013.01); *H01F 38/14* (2013.01); *A61M 2205/8243* (2013.01); *A61N 1/37229* (2013.01)

(58) Field of Classification Search
USPC ......................................................... 307/104
See application file for complete search history.

(56) References Cited

U.S. PATENT DOCUMENTS

| | | |
|---|---|---|
| 4,143,661 A | 3/1979 | LaForge et al. |
| 4,665,896 A | 5/1987 | LaForge et al. |
| 4,906,229 A | 3/1990 | Wampler |
| 4,957,504 A | 9/1990 | Chardack |
| 5,089,017 A | 2/1992 | Young et al. |

(Continued)

OTHER PUBLICATIONS

International Search Report for PCT/IL2008/000604 with a date of mailing of Jan. 30, 2009, (4 pages).

(Continued)

*Primary Examiner* — Jared Fureman
*Assistant Examiner* — Dru Parries
(74) *Attorney, Agent, or Firm* — Brown Rudnick LLP

(57) ABSTRACT

An external transmitter inductive coil can be provided in, on, or with a belt designed to be placed externally around a part of a body of a patient. An implantable device (such as a VAD or other medical device) that is implanted within the patient's body has associated with a receiver inductive coil that gets implanted within that part of the patient's body along with the device. The externally-located transmitter inductive coil inductively transfers electromagnetic power into that part of the body and thus to the receiver inductive coil. The implanted receiver inductive coil thus wirelessly receives the inductively-transferred electromagnetic power, and operates the implant.

26 Claims, 18 Drawing Sheets

(56) References Cited

U.S. PATENT DOCUMENTS

| | | | |
|---|---|---|---|
| 5,095,903 A | 3/1992 | DeBellis | |
| 5,507,629 A | 4/1996 | Jarvik | |
| 5,749,855 A | 5/1998 | Reitan | |
| 5,991,665 A | 11/1999 | Wang et al. | |
| 6,070,103 A | 5/2000 | Ogden | |
| 6,129,704 A | 10/2000 | Forman et al. | |
| 6,135,729 A | 10/2000 | Aber | |
| 6,421,889 B1 | 7/2002 | Chien | |
| 6,527,699 B1 | 3/2003 | Goldowsky | |
| 6,761,681 B2 | 7/2004 | Schmid et al. | |
| 6,772,011 B2 | 8/2004 | Dolgin | |
| 7,613,497 B2 | 11/2009 | Govari et al. | |
| 7,650,192 B2 | 1/2010 | Wahlstrand | |
| 7,741,734 B2 | 6/2010 | Joannopoulos et al. | |
| 7,783,965 B1 | 8/2010 | Dowd et al. | |
| 7,825,543 B2 | 11/2010 | Karalis et al. | |
| 7,825,776 B2 | 11/2010 | Smith et al. | |
| 7,956,725 B2 | 6/2011 | Smith | |
| 8,075,472 B2 | 12/2011 | Zilbershlag et al. | |
| 8,129,865 B2 * | 3/2012 | Krumme | A61B 6/56 307/104 |
| 8,244,367 B2 | 8/2012 | Wahlstrand et al. | |
| 8,278,784 B2 | 10/2012 | Cook et al. | |
| 8,285,388 B2 | 10/2012 | Wahlstrand | |
| 8,579,789 B1 | 11/2013 | Zilbershlag | |
| 8,585,572 B2 | 11/2013 | Mehmanesh | |
| 8,840,539 B2 | 9/2014 | Zilbershlag | |
| 8,961,389 B2 | 2/2015 | Zilbershlag | |
| 8,979,728 B2 | 3/2015 | Zilbershlag | |
| 9,343,224 B2 | 5/2016 | Zilbershlag | |
| 2004/0014315 A1 | 1/2004 | Lai et al. | |
| 2004/0054251 A1 | 3/2004 | Liotta | |
| 2004/0115038 A1 | 6/2004 | Nuesser et al. | |
| 2005/0220636 A1 | 10/2005 | Henein et al. | |
| 2007/0132587 A1 | 6/2007 | Smith et al. | |
| 2007/0182578 A1 | 8/2007 | Smith | |
| 2007/0255223 A1 | 11/2007 | Phillips et al. | |
| 2008/0041930 A1 | 2/2008 | Smith et al. | |
| 2008/0238680 A1 | 10/2008 | Posamentier et al. | |
| 2008/0292478 A1 | 11/2008 | Baykut et al. | |
| 2009/0243813 A1 | 10/2009 | Smith et al. | |
| 2010/0045114 A1 | 2/2010 | Sample et al. | |
| 2010/0052811 A1 | 3/2010 | Smith et al. | |
| 2010/0076247 A1 | 3/2010 | Zilbershlag et al. | |
| 2010/0081379 A1 | 4/2010 | Cooper et al. | |
| 2010/0187913 A1 | 7/2010 | Smith et al. | |
| 2010/0197994 A1 | 8/2010 | Mehmanesh | |
| 2011/0080051 A1 * | 4/2011 | Lee | H02J 5/005 307/104 |
| 2012/0123284 A1 | 5/2012 | Kheradvar | |
| 2012/0146575 A1 * | 6/2012 | Armstrong | H02J 7/025 320/108 |
| 2012/0150291 A1 | 6/2012 | Aber et al. | |
| 2012/0235502 A1 | 9/2012 | Kesler et al. | |
| 2012/0239118 A1 | 9/2012 | Ozawa et al. | |
| 2013/0043736 A1 | 2/2013 | Zilbershlag | |
| 2014/0163307 A1 | 6/2014 | Zilbershlag | |
| 2014/0236172 A1 | 8/2014 | Hastings et al. | |

OTHER PUBLICATIONS

Non Final Office Action mailed Sep. 26, 2016 for U.S. Appl. No. 15/097,867 (16 Pages).

Response to Non Final Office Action Filed on Oct. 14, 2016 for U.S. Appl. No. 15/097,867 (6 Pages).

* cited by examiner

COPLANAR WIRELESS ENERGY TRANSFER

RELATED APPLICATIONS

This application claims the benefit of and priority to U.S. Provisional Application Ser. No. 61/708,333, filed Oct. 1, 2012. This application is also a continuation-in-part of U.S. Nonprovisional application Ser. No. 13/588,524, filed Aug. 17, 2012, which claims the benefit of and priority to U.S. Provisional Application Ser. Nos. 61/540,140, filed Sep. 28, 2011, and 61/525,272, filed Aug. 19, 2011. The entirety of each of the above-referenced applications is incorporated herein by reference.

TECHNICAL FIELD

The present invention generally relates to wireless energy transfer into the body of a patient to power wirelessly a device implanted within the body.

BACKGROUND

Congestive heart failure results from the inability of the heart to pump blood throughout the body at its normal pace, causing blood to flow a slower rate with increased pressure. As a result, the heart is unable to meet the oxygen and nutrient demands of an individual's vital organs. Heart failure may be caused by cardiomyopathy, heart valves damage, coronary heart disease, hypertension, and, in some cases, diabetes. Worldwide, more than a million patients currently suffer from congestive heart failure. In the United States alone, thousands of patients with congestive heart failure are candidates for heart transplantation or an electromechanical heart implant, such as a ventricular assist device.

Ventricular assist devices (VAD) are implantable electromechanical pumps that are used to partially or completely replace the function of a failing heart. Ventricular assist devices do not replace the heart entirely, but rather assist the right (RVAD) or left (LVAD) ventricle in their ability to pump blood. The choice of the device depends on the underlying heart disease and the pulmonary arterial resistances, which determines the load on the right ventricle. LVADs are more common, as RVADS are typically only necessary when pulmonary arterial resistance is very high.

VADs require a power source to operate the pump. Typically, the VAD is connected to an external power source by a transcutaneous drive line. The exit site of the drive line from the abdomen provides a portal of entry for pathogens, making VAD recipients highly vulnerable to device-related infections. However infectious complications are not limited to VAD systems, as infections are common in many medical devices that use transcutaneous power line.

As an alternative to the transcutaneous power lines, wireless power transfer systems were developed to deliver power to implanted medical devices, including VADs. The traditional approach is TET (transcutaneous energy transfer), in which the energy source is directed toward the energy harvesting device with the goal to minimize RF exposure of the patient. In one commercial embodiment, the receiver coils are located under the patient's skin and the transmitter above the skin. Such TET systems are very sensitive to misalignment and movement of the implanted coil. Additionally, the coil implanted in a separate surgical procedure. Another shortcoming of the current TET solution is that the electromagnetic field density is so high that it can cause heating of the skin and even burns. That is, when the receiver is receiving energy, regular resistance losses within the coil can cause heating to the same volume of tissue receiving the electromagnetic radiation and add heating to it. When the transmitter attached to the receiver is transmitting energy, regular resistance losses within the transmitter coil can cause heating that adds to the receiver regular resistance losses heating and to the receiving electromagnetic radiation heating. The accumulated heat can become a complex issue. TET systems have also suffered setbacks due to complexity and lack of efficiency.

SUMMARY

The invention concerns coplanar wireless energy transfer (CET) systems. CET systems of the invention typically include an external transmitter coil and an implantable receiver coil coupled to an implantable medical device. The external transmitter inductive coil can be provided in, on, or with a belt designed to be placed externally around a part of a body of a patient. The external transmitter inductive coil is in communication with the internal receiver coil, as implanted, to provide wireless energy transfer to an implant device associated with the internal receiver coil. The two coils are disposed in a coplanar manner and allow for wireless energy transfer from the transmitter inductive coil to the receiver inductive coil, thereby avoiding the need for wires running inside the body from the implanted device to the under skin implant receiver as in TET system. This invention provides new approaches for medical implant wireless power transfer, which will increase the safety and efficiency, and in parallel reduce the cumbersomeness of traditional TET use by simplify the surgery and placement process.

The transmitter inductive coil can be one, two, or more turns of an electrically-conductive material such as a metal wire. The patient can be a human or an animal, and the part of the body can be the arm, leg, head, or torso of the patient. An implantable device (such as a VAD or other medical device) that is implanted within that part of the patient's body has associated with it (for example, electrically coupled to it) a receiver inductive coil that gets implanted within that part of the patient's body along with the device. The externally-located transmitter inductive coil surrounds at least a portion of the implanted receiver inductive coil and inductively transfers electromagnetic power into that part of the body and thus to the receiver inductive coil. The implanted receiver inductive coil thus wirelessly receives the inductively-transferred electromagnetic power from the external transmitter coil, and the implanted receiver inductive coil provides that received power to the implanted implantable device to allow that device to operate. If the device is a VAD, then the power can be used to operate the pumping action of the VAD.

Methods and designs for optimizing CET systems and examples of using CET for VAD or LVAD powering are also presented. In certain aspects, the invention provides methods for automatically detecting a target or resonance frequency for optimal transfer of energy from the transmitter inductive coil to the receiver inductive coil. In certain embodiments, the transmitter inductive coil is operably associated with circuitry configured to search a range of frequencies and detect the resonance frequency or a target frequency within that range. The ability to hone in on the resonance or target frequency allows one to maximize the operation efficiency of a CET system. In one embodiment, a frequency range used for wireless energy transfer into the human body is 60 KHz to 1 MHz. In preferred embodiments, the frequency used ranges from 80 KHz to 300 KHz. In further embodiments, the frequency used ranges from 90 KHz to 115 KHz.

Additionally, the invention maximizes the design and geometry of the transmitter inductive coil and/or the receiver inductive coil in order to reduce energy loss within a CET system. This includes designing the transmitter inductive coil and/or receiver inductive coil in order to avoid or minimize undesirable skin effect and proximal effect. Skin effect is the undesirable increase of wire resistance due to crowding of alternating current near the surface of the wire. Proximity effect losses occur when eddy currents are induced in one winding layer by currents in adjacent layers. Reduction of losses may be accomplished, according to certain embodiments, by using wires that are specifically designed to carry alternating currents to form the coils, such as Litz wires. The structure of those wires can also be chosen to reduce loss. In some embodiments, a wire of the transmitter inductive coil, the receiver inductive coil, or both is formed from 100 to 600 strands with a gauge ranging from 36 AWG to 48 AWG. In one embodiment, the receiver inductive coil includes 130 to 300 strands with a gauge ranging from 36 AWG to 38 AWG. In another embodiment, a wire of the transmitter inductive coil includes 175 to 400 strands with a gauge ranging from 36 AWG to 38 AWG. In addition, the number of turns of a wire that forms the coil is also provided to maximize efficiency. In one embodiment, the transmitter inductive coil includes 6 to 35 turns of a wire. In some embodiments, the receiver inductive coil includes 5 to 50 turns of a wire with a pitch of at least 0.05 inches between each turn. In other embodiments, the pitch is of at least 0.1 inches. The turns of either coil may be arranged in one or more layers, typically one, two, or three layers. Other design considerations for avoiding loss involve the ratio between the height and radius of the transmitter inductive coil. It has been found that a ratio of the height to the radius of about 0.4 to about 1.5 provides enhanced performance.

Circuits associated with the transmitter inductive coil may be designed to minimize loss and maximize efficiency of coplanar wireless energy transfer. One circuit feature is a capacitor (associated with transmitter or receiver coil) that includes an equivalent series resistance that is less than a resistance of the coil. Another feature includes associating the transmitter inductive coil with a half-bridge pulse generator. Half-bridge pulse generators, despite being square-generators, are advantageously able to generate a sinusoidal wave. In further embodiments, the receiver inductive coil is associated with an AC-to-DC rectification circuit that includes a single diode in a closed cycle. This configuration saves space within the circuitry without resulting in loss.

Placement of the transmitter inductive coil with respect to the receiver inductive coil also affects efficiency of the system. In order to provide better efficiency and less loss during energy transfer, the receiver inductive coil and transmitter inductive coil, in one embodiment, are placed such that a center of the receiver inductive coil is no more than 7 cm from a center of the transmitter inductive coil.

BRIEF DESCRIPTION OF THE DRAWINGS

In the drawing(s), like reference characters generally refer to the same or similar parts throughout the different views. The drawings are intended to illustrate the details of one or more embodiments according to the invention and/or the principles of the invention.

DETAILED DESCRIPTION

The invention relates to a wireless energy transfer system that wirelessly provides energy to an internal implant using an external transmitter inductive coil and an internal receiver inductive coil. The external transmitter inductive coil can be provided in, on, or with a belt designed to be placed externally around a part of a body of a patient. The external transmitter inductive coil is in communication with the internal receiver coil to provide wireless energy transfer to a device implanted within the body.

Figure 1:
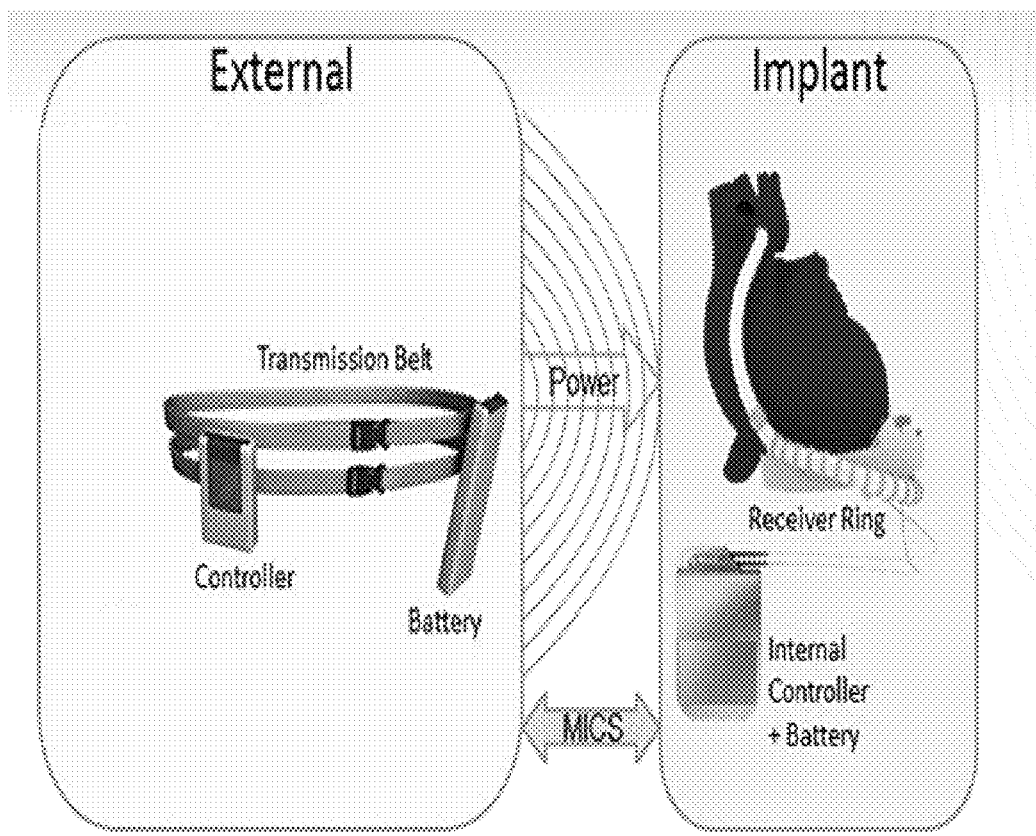
FIG. 1 is a schematic overview of coplanar wireless energy transfer according to certain embodiments.
Figure 3:
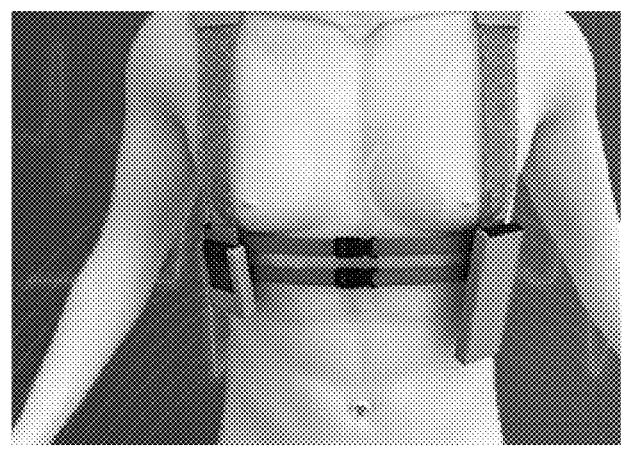
FIG. 3 illustrates an external belt (such as the belt in FIG. 1) worn by an individual.

FIG. 1 depicts a schematic overview of wireless energy transfer system of the invention. As shown in FIG. 1, the external components may include a transmission belt (which includes a transmitter inductive coil) a controller, and an external battery. The internal components include an implant (such as a ventricular assist device (VAD)), a receiver inductive coil coupled to the implant, an internal controller, and, optionally, an internal battery. The internal receiver coil is placed within the body (for example, the pericardium sack) and receives power from the external transmission belt. FIG. 3 depicts the external transmission belt disposed an individual's torso, and is ideally placed for transmitting power to an implant in the pericardium sack. The internal controller controls is associated with the receiver, controls power reception circuits, activates the implant electronics, and communicates with the external controller. The internal battery provides back-up power and enables operation of the implant independent of the wireless power transfer. The transmission belt includes a transmitter coil, and transmits power to the internal receiver coil via a magnetic coupling. The external controller can run power transmission algorithms (described hereinafter), communicate with the implant (e.g. through the frequency band of the Medical Implant Communication Service (MICS), which includes frequencies between 402 and 405 MHz), and push power to the belt from the battery. The external battery is able to provide power to the transmission, and allow for generation of the electromagnetic field.

This physical arrangement of the external surrounding transmitter coil and the internally implanted receiver coil (that is disposed at least partially within an imaginary plane cutting through the patient's body and that is formed or defined by the surrounding external transmitter coil) can be referred to as a coplanar arrangement. And the system of the external transmitter coil and the implanted receiver coil thus can be referred to as a coplanar energy transfer (CET) system.

CET is different than a known and common technique referred to as transcutaneous energy transfer (TET). TET only transfers energy through an area of the skin of a patient to a shallowly-implanted receiver just under that area of the skin. CET, in sharp contrast, involves surrounding the implanted receiver coil by placing or wrapping a transmitter coil completely around the part of the patient's body within which the receiver coil is implanted. If the receiver coil is disposed within the brain of the patient, for example, then CET involves disposing the transmitter coil externally around the corresponding part of the head of the patient such that an imaginary plane defined by the surrounding transmitter coil extends through at least a portion of the brain-implanted receiver coil. If the receiver coil is instead implanted within the descending aorta of the patient's vasculature, CET involves disposing the transmitter coil externally around the corresponding part of the patient's chest such that the imaginary plane defined by the surrounding transmitter coil extends through at least a portion of the aorta-implanted receiver coil. These are just two examples of where the transmitter and receiver coils could be located, and other locations are possible such as the arm or the leg of a patient.

Figure 2:
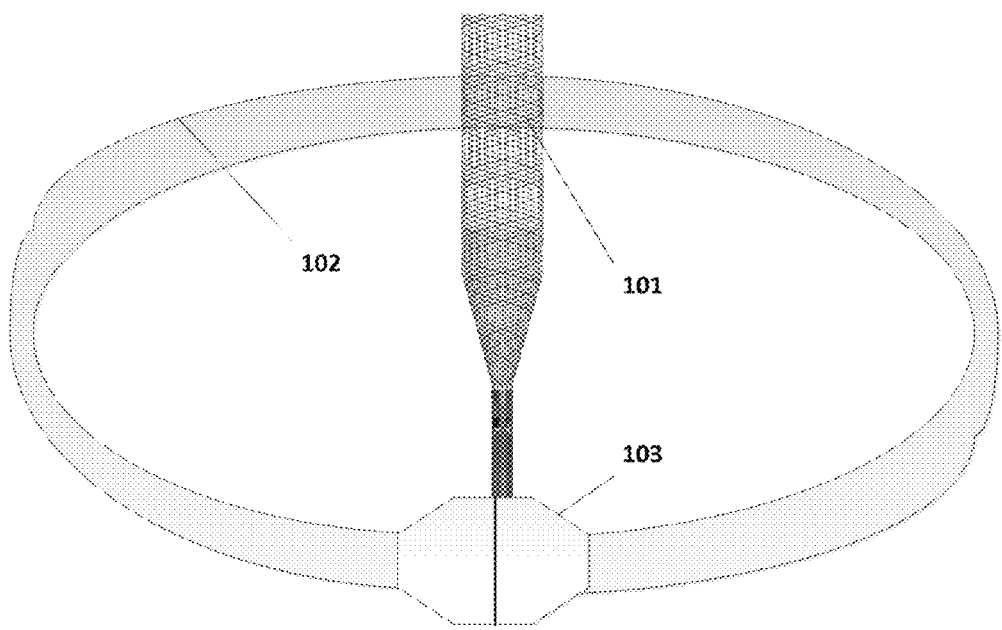
FIG. 2 depicts an external belt 102 surrounding an implantable receiver coil 101; the belt can be opened and closed using a buckle 103.

FIG. 2 depicts another view of the coplanar energy transfer system of the invention (also referred to as CET systems). Referring to FIG. 2, a surrounding belt 102 is depicted with a medical stent 101 therewithin. The stent 101 has built into it or incorporated within it a receiver coil of one or more turns of electrically-conductive material such as copper wire, for example. The belt 102 has in or on it, around its entire length, one or more turns of a transmitter coil Like the receiver coil, the transmitter coil can have one or more turns of electrically-conductive material such as copper wire, for example. Together, the external belt 102 with the transmitter coil and the implantable medical device (such as a stent) with the receiver coil, can be considered a wireless power transfer system. In use, the transmitter coil can be located externally around the chest of a patient or around some other part of the patient's body such as an arm, a leg, a head, or another part of the patient's torso, and the receiver can be implanted within that part of the patient's body, such that electromagnetic power inductively transmitted from the surrounding coil of the belt 102 reaches and is wirelessly received by the patient-implanted receiver coil from all angles and directions.

The stent 101 of FIG. 2 has built into it or incorporated within it the receiver coil, as indicated previously, and in this regard it is noted that the receiver inductive coil can comprise one or more electrically conductive fibers or strands that are among the various fibers or strands that together constitute the stent 101. These fibers or strands that comprise the receiver inductive coil can be electrical wires and can be coated with an electrical insulator. The receiver inductive coil can be built into or incorporated within the stent 101 in a variety of other ways.

In one embodiment, the receiver coil is not built into the device with which it is associated. In this embodiment, the implantable receiver coil is operatively connected (such as by an electrical wire connection) to the implantable device in order to provide wirelessly-received power to the implanted device. The implantable receiver coil can otherwise be physically separate from and not an integral part of the device itself. In another embodiment, the receiver coil is built into the device with which it is associated. In one embodiment, the receiver coil is a stent 101 as shown in FIG. 2 as the device with which the implantable receiver coil is associated.

In addition to VADs, the receiver coil can be associated with a variety of other types of implantable devices, including, for example, a constant glucose meter (CGM), a blood-pressure sensing device, a pulse sensing device, a pacemaker, implantable cardioverter defibrillators (IDC), digital cameras, capsule endoscopies, implanted slow release drug delivery systems (such as implanted insulin pump) a nerve stimulator, or an implanted ultrasound device.

In operation, the CET system generates lower radio-frequency (RF) energy densities than TET systems. Because CET uses a surrounding external belt-like transmitter coil, the RF energy that is inductively transmitted into the patient's body from the transmitter coil is spread out and not concentrated or focused into or onto a particular spot or area of the patient's body. Using CET, the transmitted energy is spread out over the external transmitter coil of the CET, resulting in transmitted field strength and power density levels that are lower than TET systems. Also using a surrounding external belt-like transmitter coil eliminate misalignment problem and reduce dramatically the misplacement problems.

It is noted that a power source must be associated with the external transmitter coil to provide that coil with the power that it will then wirelessly transmit for receipt by the implanted receiver coil. A controller unit also typically will be provided to regulate the operation of the transmitter coil Like the transmitter coil, both the power source and the controller will be external to the patient. The external source can be an AC current source, and the transmitter coil can be electrically connected to the AC current source. It also is noted that the transmitter coil can be a transmitter—that is, capable of both transmitting and receiving.

Providing an Optimal Load to the Receiver Resonance Structure:

In one embodiment according to the invention, the device with which the implantable receiver coil is associated is a ventricular assist device (VAD). In this embodiment a DC-to-DC converter is employed to provide an optimal load to the receiver inductive coil. The DC-to-DC converter is designed to automatically adjust to provide a constant or substantially constant selected optimum load to the receiver inductive coil. Typically, the DC-to-DC converter is implanted within the patient's body along with the receiver inductive coil and the VAD.

Figure 4:
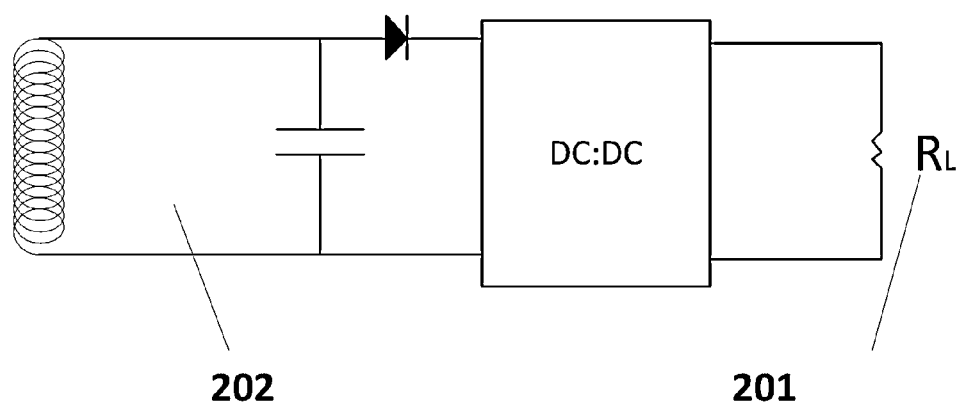
FIG. 4 shows an implantable circuit with a DC-to-DC converter coupled to the implantable receiver resonance structure 202. The load $R_1$ can be a VAD or any other power consuming implantable device.

FIG. 4 shows a DC-to-DC converter disposed between the receiver inductive coil and the resonance structure 202 (on the left) and a load $R_L$ (on the right). Load 201 may be a VAD or a constant glucose meter, or another implantable device described herein. As shown in FIG. 4, the circuit can also include a half or full-wave rectification (i.e., using a diode or diode bridge). As shown in FIG. 4, resonance structure 202 is formed by the receiver inductive coil and a capacitor. However the external transmitter inductive coil may also be associated with a capacitor to form a transmitter or transmitter resonance structure. A resonance structure of the transmitter can be the same as or different from the receiver.

Figure 5:
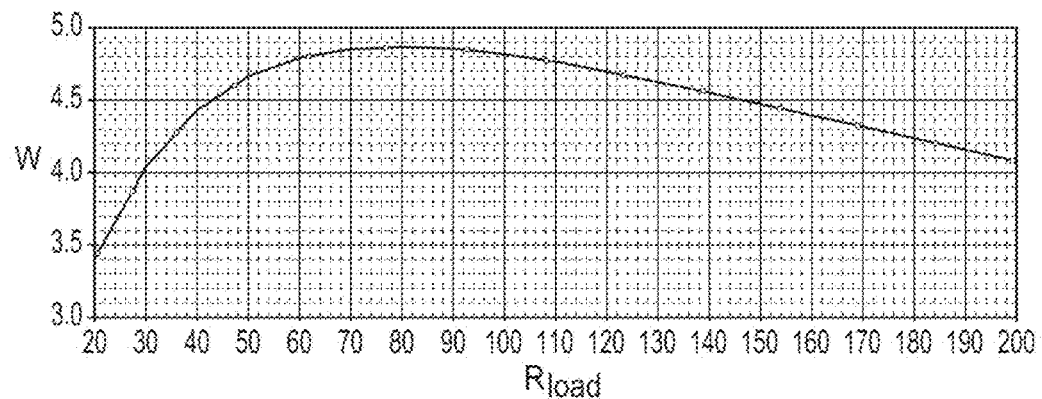
FIG. 5 is a graph showing a relationship between output power and load resistance.

The optimum load can be determined with reference to FIG. 5 which shows a relationship between power harvesting (W) and an $R_{load}$ value for a particular circuit, where $R_{load}$ is the internal resistance of whatever load is associated with the receiver inductive coil. While merely exemplary, the graph of FIG. 5 shows that the best power harvesting for the circuit is 80 Ohms or about 80 Ohms. A load with a resistance lower than 80 Ohms will reduce the voltage on the load and thereby reduce the harvested power, and a load with a resistance higher than 80 Ohms will reduce the current and thereby reduce the harvested power. The shape of the curve in the graph of FIG. 5 is determined by the function (26), provided below. In the case of a VAD, the resistive load represented by the VAD's motor will change as the mechanical load on the motor changes, and the depicted circuit (in FIG. 4) with the DC-to-DC converter is what is used to automatically adjust and provide a substantially constant and optimum load to the receiver inductive coil.

Figure 6:
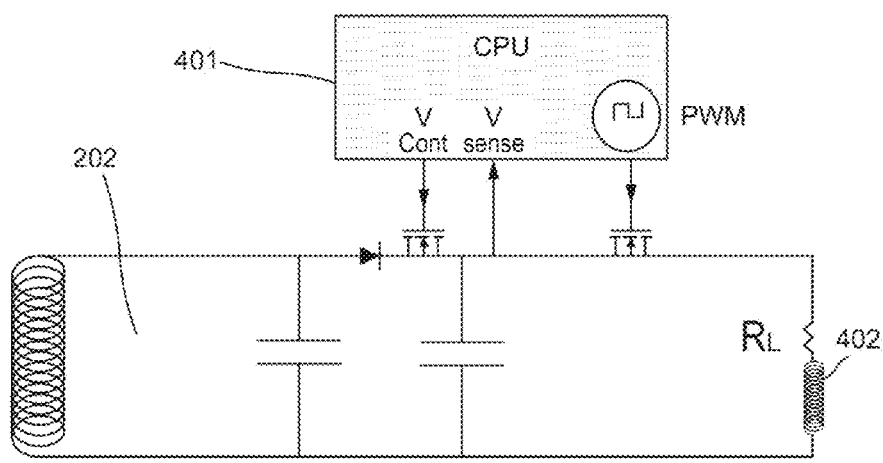
FIG. 6 shows an alternative circuit coupled to the implantable receiver coil. The circuit has the same resonance structure 202 but uses the inductiveness of the implant VAD 402 and controller 401 as a DC to DC.

In case of medical implant with high inductive load, like a VAD or implanted slow release drug delivery system that uses a motor, an alternative to the circuit of FIG. 4 is the circuit shown in FIG. 6. The circuit of FIG. 6 can be employed to adjust to an ideal working point of the receiver inductive coil (or, more accurately, of the receiver resonance structure which, as described above, is the combination of the receiver coil and its associated capacitor) when the device with which the implantable receiver coil is associated is a VAD.

An implant with a brushless DC motor, like a VAD, needs adjustable power control to receive exactly the needed mechanical power. As shown in FIG. 5 and by function (26) below and as described above, the best power harvesting is achieved with the optimum $R_{load}$. In this situation, a high quality motor controller, such as MOTION EN Speed Controller Series SC 1801 F (Faulhaber GmbH & Co. KG, Schonaich, Germany), can be used as a DC-to-DC converter for adjusting the $R_{load}$ to the optimum value using PWM (pulse width modulation). As shown in FIG. 6, a voltage and motor PWM controller 401 gives full control over the working point without any additional measures.

By controlling the voltage and the DC-to-DC rate, the optimum $R_{load}$ can be achieved. The brushless DC motor of the VAD can be simulated with an equivalent resistor and inductor circuit. The speed of the motor is controlled using PWM as the motor input voltage, and the duty cycle is adjusted according to the needed speed. The coils of the VAD's motor flat the current just as is done in DC-to-DC voltage conversion. In this way, the VAD's motor is used as a DC-to-DC converter, and the reflected motor load is dependent on the conversion rate.

Adding a voltage sensor with voltage control adds the capability to select the voltage in the receiver circuit. This gives full control on the reflected load (using the PWM mechanism) and on the used power by controlling the voltage (using the voltage control). For example, a LPC1102 chip can be used for (NXP Semiconductors N.V., Eindhoven, Netherlands) voltage sensing while an internal PWM engine and can control the voltage by using a transistor like SI8409 DB (NXP Semiconductors) for closing the inline from the resonance structure 202.

The voltage control can be done in several ways. One example is harvesting control on/off measured, as shown in FIG. 6, in the implanted receiver electronics itself. Another example is transmitting power control in the external transmitter/transmitter primary electronics that closes the loop according to the $V_{sense}$ in the receiver.

Locking the Receiver and the Transmitter:

Once placed within the body of a patient, the receiver coil shape can be distorted or modified from its at-rest shape and also can move over time to some extent as the patient moves, all depending on the particular location internally within the patient's body where the receiver coil is placed. With changing of its shape, the resonance frequency of the receiver coil changes. It is important for the transmitter resonance structure to be able to automatically find the receiver's resonance and adjust the transmitter's resonance to that found for the receiver and lock to that found resonance. In other words, the transmitter must have the capability to detect the receiver's resonance frequency and then lock to that detected receiver's resonance frequency.

Figure 16:
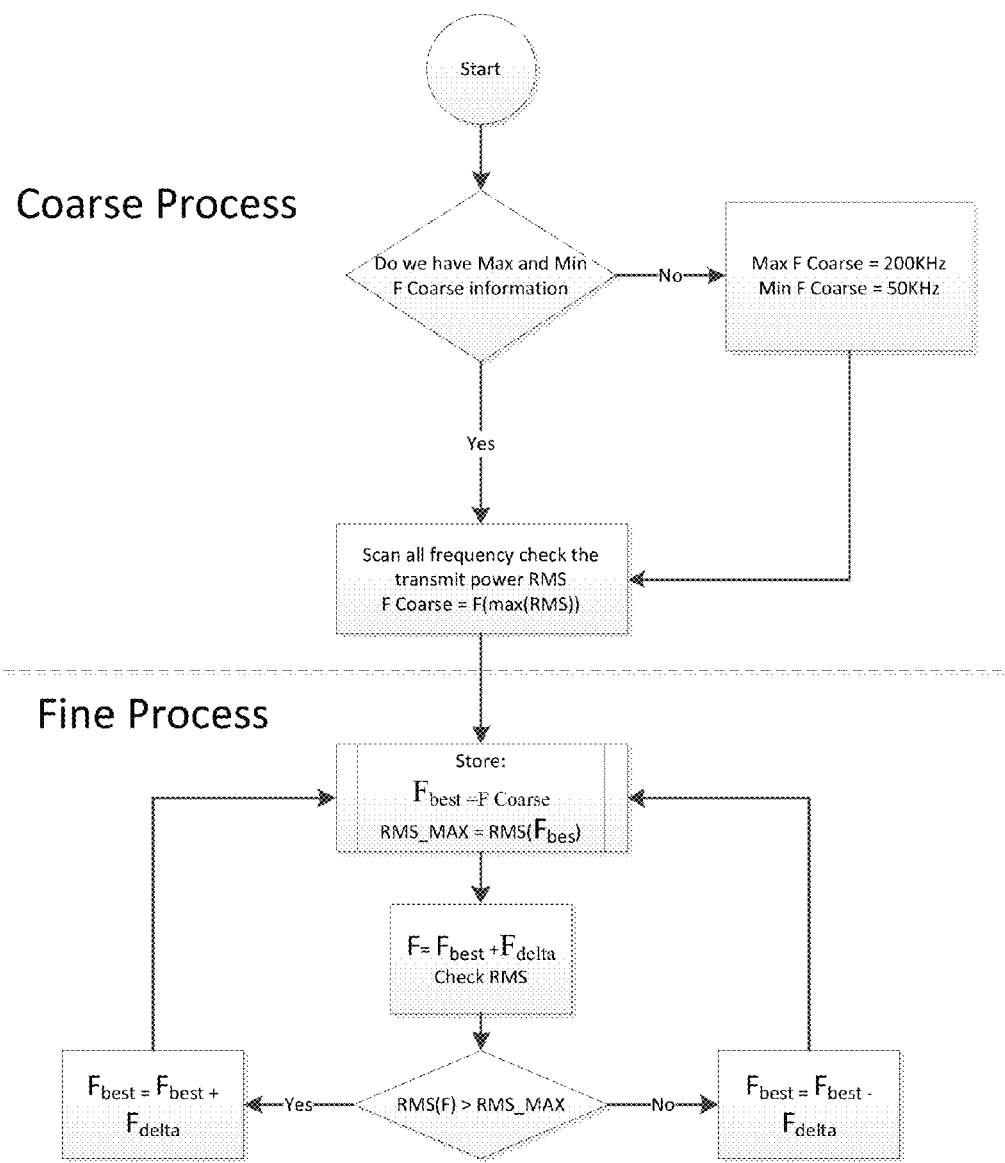
FIG. 16 is a flow chart of coarse and fine resonance frequency detection.
Figure 17:
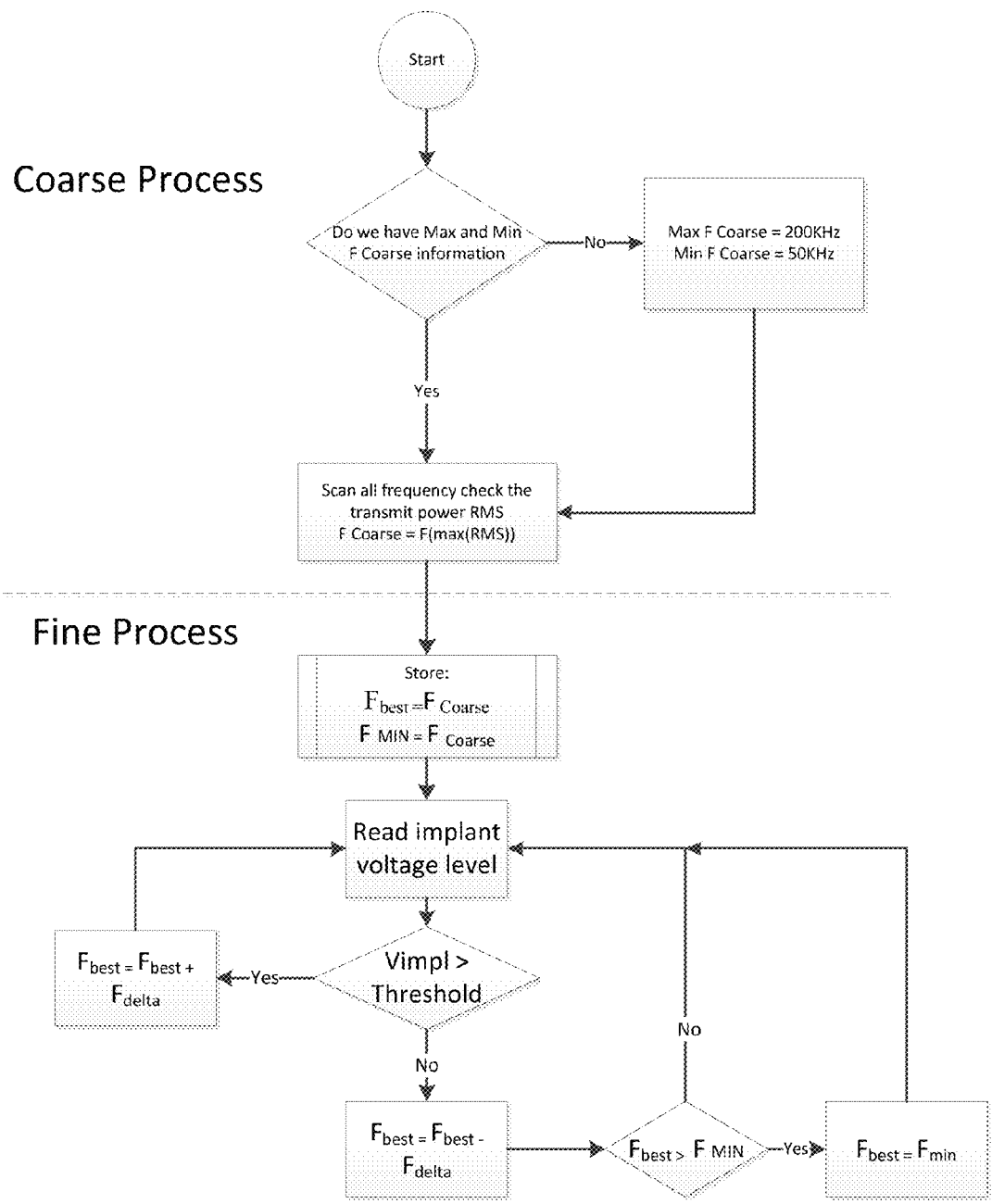
FIG. 17 is a flow chart of coarse and fine frequency base power control.
Figure 18:
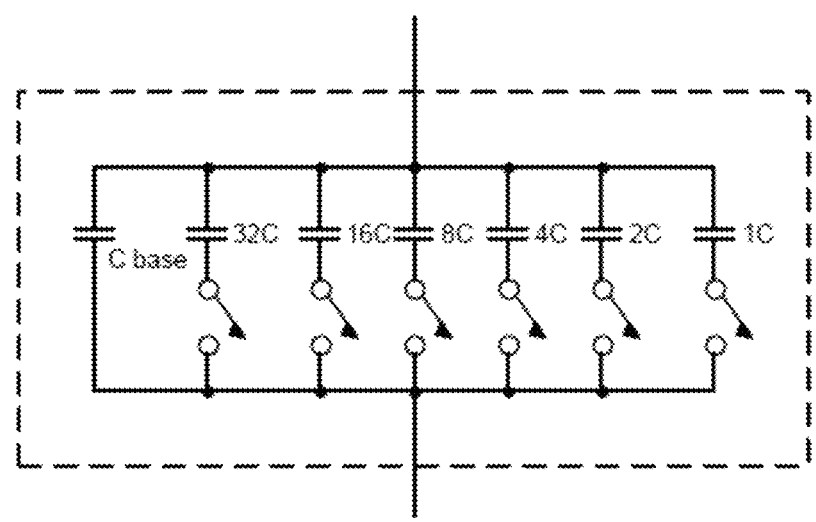
FIG. 18 shows a configurable capacitor for use with a circuit for locking the external transmitter resonance.

As described in FIG. 16 and in FIG. 17 the transmitter can detect the receiver's resonance frequency in two phases. First, in a coarse phase, when no pre-detected frequency is available, the transmitter uses a fast frequency detection process to roughly detect the receiver resonance frequency or else just start at some predetermined frequency. Second, in a fine phase that occurs after the coarse phase, the transmitter uses an ongoing process of fine tuning to detect the receiver resonance frequency.

The main difference between the two procedures is the simplicity of the solution. FIG. 17 describes a very simple system where the coarse phase detects roughly the resonance, which then becomes the minimum frequency limit. (The system doesn't use the resonance frequency exactly, it uses a frequency above (or below) the resonance and then controls the transfer power by tuning the frequency). This is a simple system and it can work in strong coupling environment like the CET system. In other instances, when the coupling is lower due to distance or receiver/transmitter size/quality it is necessary to use the exact resonance frequency to be able to transfer the needed power.

FIG. 16 describes the fine process that occurs after the first coarse adjust approximately determines the transmitter resonance. In the coarse phase, a microcontroller (MCU) associated with the transmitter resonance structure can have preliminary information about the receiver resonance frequency. The MCU will change the transmitter's driver frequency one after the other and detect the root mean square (RMS) current in the one or more coils of the transmitter. At the end of this phase, the MCU has the result of the entire frequency spectrum, and it can automatically select (as a result of its software programming) the best first coarse frequency, $F_{coarse}$.

After the coarse phase, the fine phase begins, in which the MCU's software programming dictates the selected frequency from the coarse phase as the best known resonance, $F_{best}$. Once in the fine phase, the MCU stores the RMS current, adds single $F_{delta}$ to the previous frequency and stores that RMS current. By comparing these two RMS currents, the transmitter's MCU determines whether to add $F_{delta}$ or to reduce $F_{delta}$ from the previous $F_{best}$. The equation used is as follows: $F_{best}=F_{best}+/-F_{delta}$. Then, the transmitters' resonance frequency is locked to the receiver's resonance frequency until the next fine phase process occurs. The fine phase process can occur periodically every $T_{fine}$.

Figure 7:
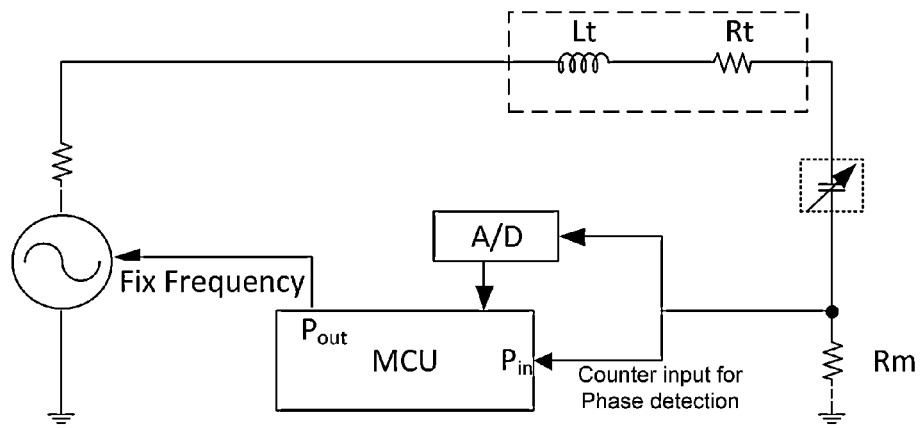
FIG. 7 is a circuit that can be used to lock the external transmitter resonance frequency to the implanted receiver resonance frequency.
Figure 8:
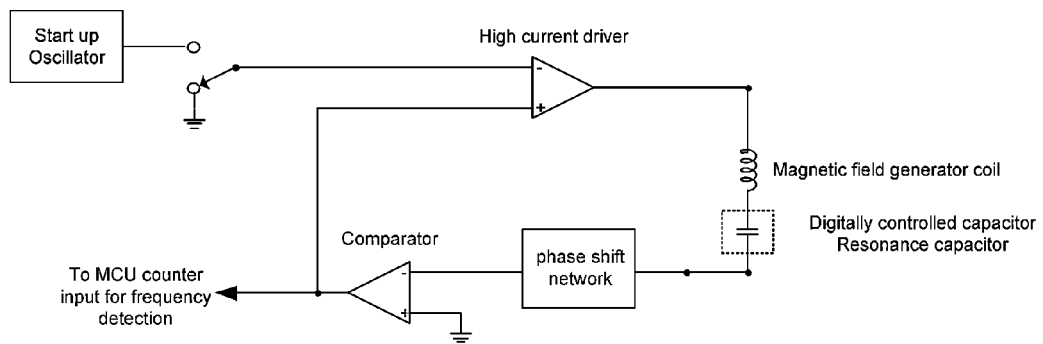
FIG. 8 is another circuit that can be used to lock the external transmitter resonance frequency to the implanted receiver resonance frequency.

Locking the transmitter resonance to the detected receiver resonance involves the transmitter coil automatically adjusting its capacitors, which can be accomplished using either the circuit shown in FIG. 7, or the circuit shown in FIG. 8, each of which is a resonance LC (inductance and capacitance) structure.

In the circuit of FIG. 7, the MCU forces a fix frequency by generating $P_{out}$ pulse in the requested frequency and push the driver circuit. In so doing, the MCU thereby calibrates the configurable capacitor to get resonance. The MCU receives the feedback phase, and adjusts it to the resonance. In resonance, the feedback phase $P_{in}$ should be exact as the generated one $P_{out}$. The MCU then compares the output $P_{out}$ to the input $P_{in}$ to validate the resonance. The MCU should adjust the capacitors according to the phase until $P_{in}=P_{out}$ In the circuit of FIG. 8, the circuit is a self-oscillating circuit, and thus is always in resonance; however the MCU can adjust the frequency by changing the capacitors. The MCU can add capacitors to the capacitors array or remove capacitors as described in FIG. 16.

Although FIGS. 7 and 8 show two particular circuits that can be used, it is noted that a variety of variants of phase locked loop (PLL) algorithms and implementing circuits can be used to compensate for impedance changes of the coils by adjusting capacitor value.

Figure 19:
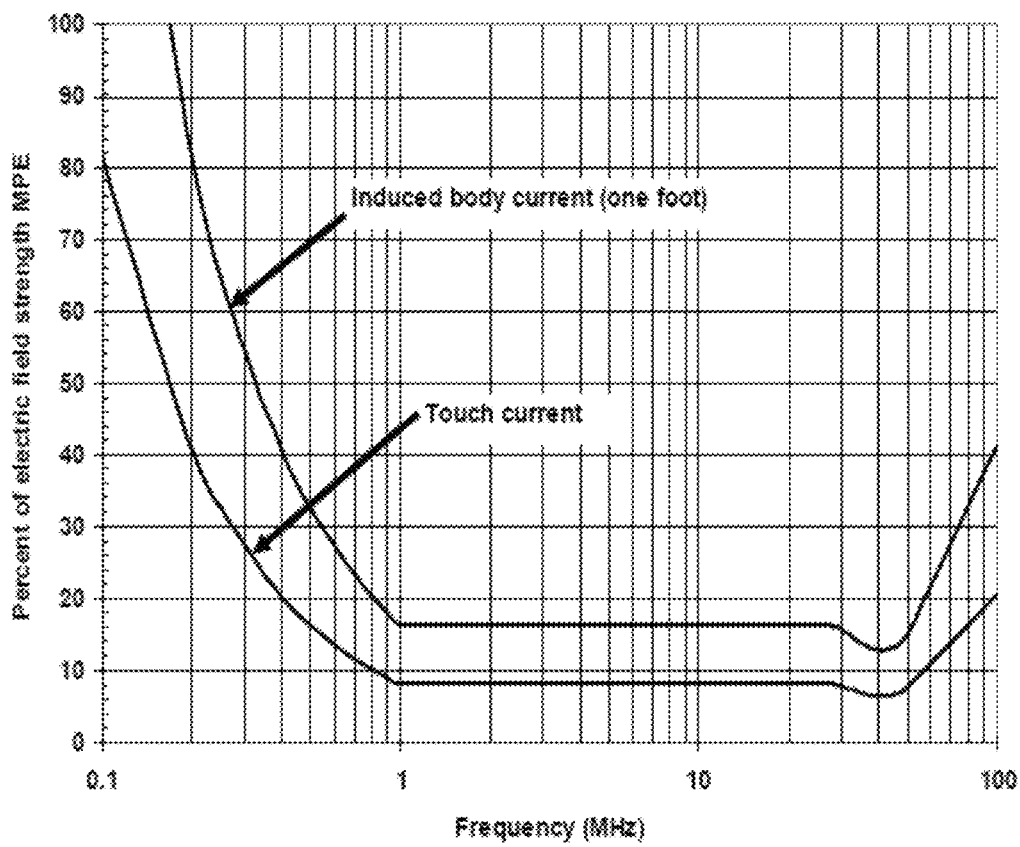
FIG. 19 exemplifies frequencies that can cause tissue heating.

Optimizing Frequency of the Power Transfer:

Wireless energy transfer to an implanted medical device, e.g. CET, requires consideration of two parameters, namely (1) the effect of wireless energy transmission on the living tissue through which it is transmitted and (2) the loss in efficiency of the wireless energy transfer due absorption by the living tissue. Other limitations of energy transfer are energy ranges deemed injurious to tissue, as in the ranges set forth in the IEEE Standard C95.1. For example, ranges 3 kHz to 5 MHz can cause painful electro stimulation; 100 kHz to 300 GHz can cause tissue heating (as shown in FIG. 19); and 100 kHz to 5 MHz can cause both electro stimulation and tissue heating. With those parameters and limitations taken into consideration, the optimal frequency of power transmission between a transmitter coil and a receiver coil of the invention provide for high power efficiency and high power transmission without any associated undesirable tissue heating. FIG. 19 shows a percent of electric field strength MPE in the induced body current (of one foot) and the touch current at certain frequencies.

CET systems of the invention achieve optimal energy transfer (such as electromagnetic power) by employing frequencies ranging from 60 KHz to 1 MHz. In that range, the preferred frequency may range from 80 KHz to 300 KHz. In other embodiments, the preferred frequency may range from 90 KHz to 115 KHz. Using frequencies within that range, systems of the invention provide for high power efficiency and high power transmission without any associated undesirable tissue heating.

CET systems of the invention may be programmed to search for a target frequency in order to optimize the functional conditions. This search may be automatic. For the search, the system may utilize circuitry—e.g. a microcontroller (e.g., as in FIGS. 7 and 8), a phase-locked loop circuit (as with analog circuits), or other processor—associated with the transmitter to search and detect the certain frequency of the receiver coil and lock the frequency of the transmitter coil to the receiver coil. The search circuitry controls the transmitter frequency according to input. Depending on the application, the certain frequency may be the resonance frequency or a non-resonance frequency.

The search circuitry may utilize several loop input measurements in order to detect the certain frequency. In addition, the search circuitry may rely on the same principles discussed above to detect the frequency of the receiver and lock the frequency of the transmitter to the receiver. The loop input measurements include, for example, the transmitter power, the receiver power, or other parameters such as an implant current parameter, an implant voltage parameter, an implant charging parameter, a hit parameter, etc. When utilizing transmitter power as an input measurement, the system detects the mutual resonance frequency of the transmitter and receiver at the point where the current in the transmitter inductive coil is maximized. In embodiments that utilize the transmitter power, the circuitry required for the search can be self-contained on the transmitter, and no communication is required from the receiver. When utilizing receiver power as an input measurement, the system detects the mutual resonance frequency of transmitter and receiver at the point where the power within the receiver is maximized, which can be sensed from the current with or without voltage in the receiver circuit. In embodiments that utilize the receiver power or receiver parameters for the search, a microcontroller or other circuitry should also be associated with the receiver to obtain measurements and allow for communication from the receiver to the transmitter.

For resonance frequency searching, the search is initiated by the transmitter circuit. The search utilizes a loop to locate the best frequency with one of the input measurements based on the transmitted efficiency, which is indicated by the current in the transmitter. The search goes down (or up) a range of frequencies (such as the dynamic band), and the resonance frequency is detected because it provides peak efficiency. That is frequencies before and after the resonance frequency are not as efficient, thereby allowing the system to detect the resonance frequency.

For non-resonance frequency searching, the search is initiated by the transmitter circuit. The search utilizes a loop to locate a target frequency with one of the input measurements based on the transmitted efficiency, which is indicated by the current in the transmitter. The search goes down (or up) a range of frequencies, and will stop when it reaches the desired efficiency.

By not operating on the resonance frequency, the system is able to control power by manipulating the frequency. For instance, in some CET systems, the desired frequency is 98 KHz just above ideal the resonance frequency of 97.4 KHz. This allows power transfer control simply by changing the frequency. In those instances, the system transmits high power when using a frequency near the resonance and low power when using frequencies farther from resonance.

The resonance and non-resonance frequency searches may be conducted across a dynamic band of frequencies. The dynamic band is the general search range of frequencies. The search typically ends at lowest frequency in the dynamic band. The dynamic band may range from 80 KHz to 140 KHz. The lowest frequency in the dynamic range may be a frequency where no resonance is found. If a system reaches the lowest frequency within the band without finding a resonance frequency of the receiver, the system may terminate the search and may trigger an alarm sound. For example, if 80 KHz is the lowest frequency in the dynamic band, the system will search within the frequency range from the highest frequency to the lowest frequency. In certain embodiments, the search will terminate and an error alarm will sound if the system search reaches the lowest frequency of 80 KHz without finding the resonance frequency of the receiver.

Typically, resonance and non-resonance frequency searches will start at a higher frequency of a dynamic band (e.g., about 140 KHz), and then adjust the search downward towards the resonance or target frequency until the resonance or target frequency is detected. For non-resonance searching, the target frequency may be within range of frequencies called the target main frequencies, which are frequencies desired and targeted by the CET system for optimal efficiency. In certain embodiments, the target main frequency range is from 90 KHz to 115 KHz. It is understood that other frequencies can be used as for the dynamic band and target main frequencies depending on the application (e.g. depending on the selected frequency range).

Figure 20:
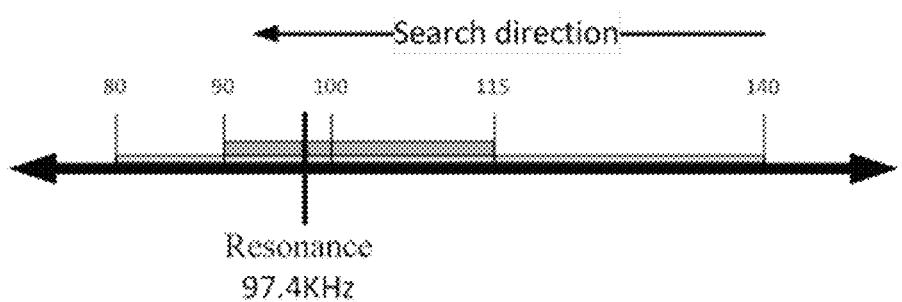
FIG. 20 depicts dynamic band of frequency used to search for resonance or target frequency.

The following describes using the dynamic band to search for a resonance or target frequency in accordance with FIG. 20. Circuitry associated with the transmitter conducts a search of a dynamic band of frequencies ranging from 140 KHz to 80 KHz. The dynamic band of frequency overlaps with the range of target main frequencies (ranging from 90 KHz to 115 KHz), with the resonance frequency being 97.4 KHz. The transmitter will start search at the top of dynamic band at 140 KHz and then adjust to lower frequencies until the resonance frequency is found or a target frequency within the range of target main frequencies is reached. When conducting a resonance search, the system will initiate an alarm if the search does not find the resonance frequency when it reaches the lower limit of about 80 KHz.

Figure 9:
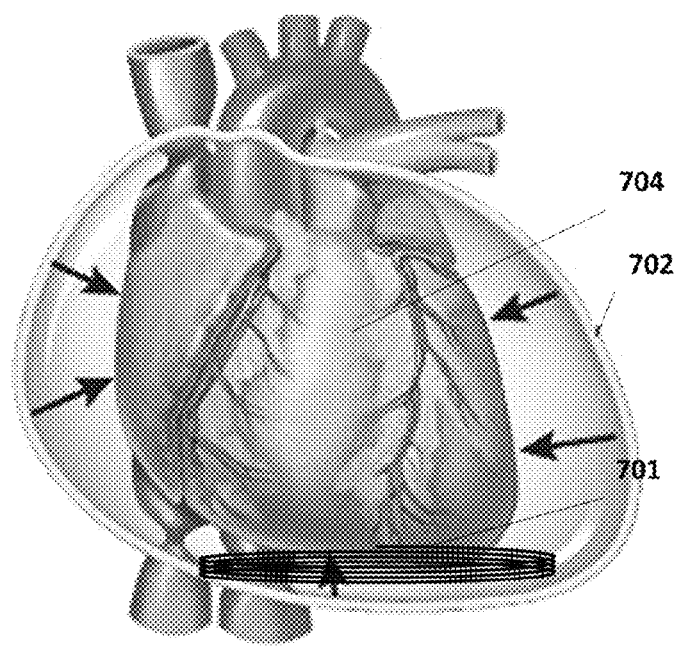
FIG. 9 shows ring coil 701 implanted in the bottom of the pericardium sack 702.
Figure 10:
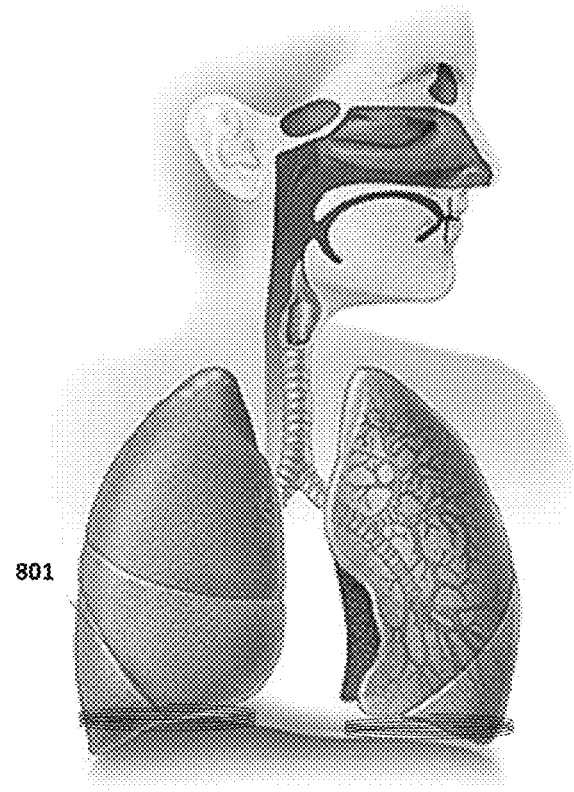
FIG. 10 shows two ring coil 801 implanted in the bottom of the pulmonary cage.
Figure 11:
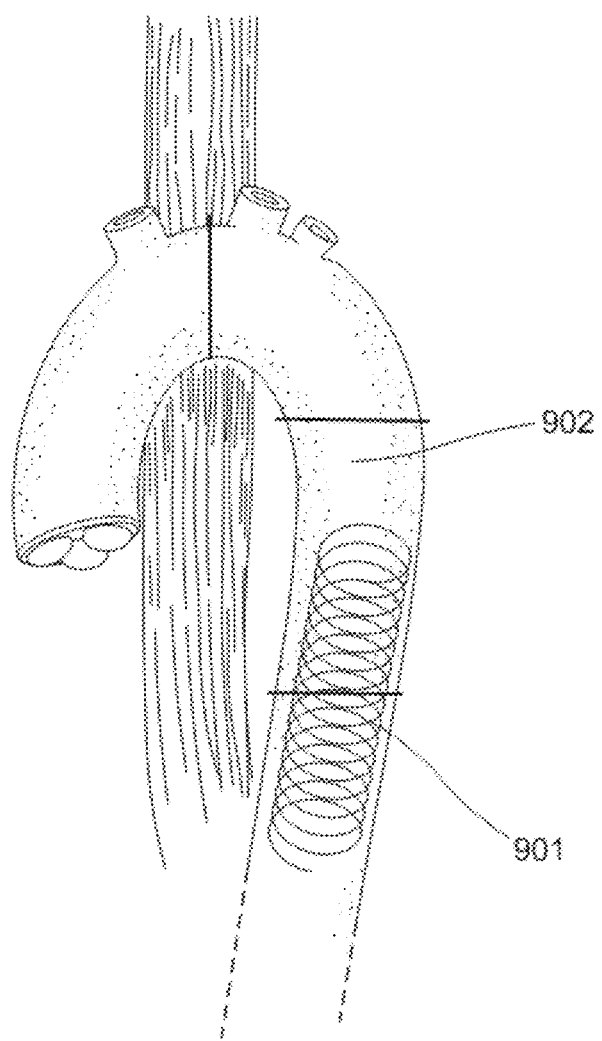
FIG. 11 shows stent base ring coil 901 located in the descending aorta 902.

Placement in a Patient's Body of the Receiver Resonance Structure:

The receiver inductive coil can be placed within the body of a patient at a variety of internal locations. FIGS. 9, 10, and 11 illustrate three particular examples of a placement location inside the body of a patient.

As shown in FIG. 9, the receiver coil 701 may be placed in the base of the flat part of the pericardia 702, which surrounds the heart 704. The main added value in placing the receiver coil 701 in the pericardia 702 with a VAD is that the pericardia 702 is relatively flat and open in typical VAD surgery. The receiver coil 701 can be glued to the pericardia 702 boundaries, e.g., with surgical glue.

In FIG. 10, it is shown that the receiver coil 801 of a VAD can be placed in the pulmonary cage. One advantage of placing the coil 801 in the pulmonary cage is that the VAD will not disturb the magnetic power harvesting, and that pulmonary cage is relatively easy to access during the VAD surgery.

As shown in FIG. 11, the receiver coil 901 may also be placed in an artery 902. The Aorta or the Vena Cava are particularly well-suited for placement of the receiver coil 901 because each is oriented vertically with respect to a plane that cuts in a cross section through the torso of the patient. Placement of the receiver coil 901 in the Aorta or the Vena Cava also allows the receiver coil 901 to be associated with an implantable stent.

Further Disclosure Related to Providing an Optimum Load to the Receiver Resonance Structure:

Having presented various details of various embodiments according to the invention, some theory, equations, and calculations relevant to providing an optimum load to the receiver resonance structure will now be presented.

The ratio between the distance D from the transmitting coil to receiving coil and the wavelength λ is as follows:

$$\frac{D}{\lambda} = \frac{Df}{c}, \quad (1)$$

where f is the transmitting frequency and $c=3 \cdot 10^8$ m/s is the speed of light.

Given that the maximum distance $D_{max}$ does not exceed 0.4 m and the working frequency is f=100 kHz, the ratio $D_{max}/\lambda = 0.00013 \ll 1$. Thus, we can conclude that the receiving coil is in the quasi-static area, and we can neglect the effects of the phase difference due to the wave propagation.

The amplitude of the voltage induced in the receiving coil according to the Faraday's law [1] is as follows:

$$v_r(t) = -\frac{d\Phi}{dt} = -\frac{d}{dt}(B \cdot a), \quad (2)$$

where Φ is the magnetic flux through the receiving coil, B is the magnetic flux density, and a is the effective area of the receiving coil.

To estimate the maximum induced voltage (2), assume that the receiving coil is located coaxially with the transmitting coil at its center, where the magnetic flux density B can be calculated as follows [1]:

$$B = \frac{\mu_r \mu_0 I_t N_t}{2R_t} \sin(2\pi f t), \quad (3)$$

where $\mu_r$ is the relative permeability of media, $\mu_0 = 4\pi 10^7$ V·s/(A m) is the permeability of vacuum, $I_t$ is the amplitude of the current in the transmitting coil, and $R_t$ and $N_t$ are the radius and number of turns of the transmitting coil correspondingly.

The effective area of the receiving coil can be calculated as follows:

$$a = \pi R_r^2 N_r, \quad (4)$$

where $R_r$ and $N_r$ are the radius and the number of turns of the receiving coil correspondingly.

Substituting (3) and (4) into (2) and differentiating with respect to the time, gives the following expression for the amplitude of the voltage induced in the receiving coil:

$$V_r = 2\pi f \frac{\mu_r \mu_0 I_t N_t}{2R_t} \pi R_r^2 N_r. \quad (5)$$

The transmitting and the receiving coils can be seen as two coupled inductors, as follows:

$$\begin{cases} v_t = L_t \frac{di_t}{dt} - M \frac{di_r}{dt} \\ v_r = -M \frac{di_t}{dt} + L_r \frac{di_r}{dt}, \end{cases} \quad (6)$$

where $v_t$ and $v_r$ are the transmitter and receiver coils voltages, $i_t$ and $i_r$ their currents, and M is the mutual inductance.

Assuming that the current in both coils is a sine-wave of frequency $\omega = 2\pi f$, (6) can be written as follows:

$$\begin{cases} v_t = j\omega L_t i_t - j\omega M i_r \\ v_r = -j\omega M i_t + j\omega L_r i_r. \end{cases} \quad (7)$$

The mutual inductance M can be found from the open circuit experiment, where $i_r = 0$:

$$\begin{cases} v_t |_{i_r=0} = j\omega L_t i_t \\ v_r |_{i_r=0} = -j\omega M i_t. \end{cases} \quad (8)$$

Rearranging the second equation of (8) with respect to M and substituting (2)-(5) gives us:

$$M |_{i_r=0} = -\frac{v_r}{j\omega i_t} = -\frac{-\frac{d}{dt}(B \cdot a)}{j\omega i_t} = \frac{\mu_r \mu_0 N_t}{2R_t} \pi R_r^2 N_r = 3.9 \ \mu H. \quad (9)$$

The value of M obtained in (9) increases as a function of the relative permeability $\mu_r$ of the receiver core.

Figure 12:
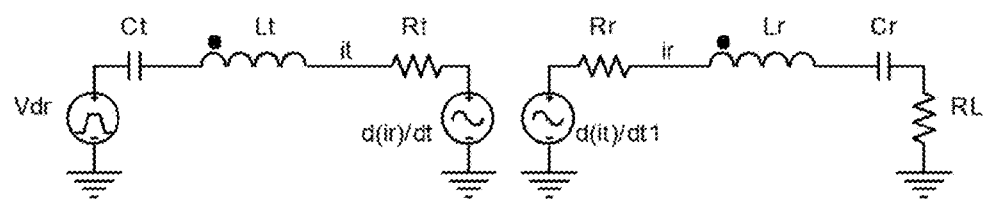
FIG. 12 shows a model circuit for calculating the efficiency of energy transmission.

For the purpose of efficiency calculation, assume that the transmitter coil is loaded with a series resonant capacitor and the receiver coil is loaded to form a series resonant circuit as describe in FIG. 12.

The transmitter current is calculated using the coupled-inductor model (7), as follows:

$$i_t = \frac{v_s}{R_t + \frac{(\omega M)^2}{R_r + R_L}}, \quad (24)$$

where $v_s = 2V_{DD}/\pi$ is the effective voltage of the source $V_{dr}$ at the first harmonic of the excitation frequency, $R_t$ is the active resistance of the transmitter coil, $R_r$ the active resistance of the receiver coil, and $R_L$ is the load resistance.

The amplitude of the load voltage is given by:

$$V_L = \frac{2\omega M V_{DD}/\pi}{R_t + \frac{(\omega M)^2}{R_r + R_L}} \cdot \frac{R_L}{R_r + R_L} = \frac{2\omega M V_{DD}/\pi}{R_t(R_r + R_L) + (\omega M)^2} \cdot R_L, \quad (25)$$

where $V_{DD}$ is the supply voltage of the half-bridge driver of the transmitter.

From here, the load power is given by:

$$P_L = \frac{V_L^2}{2R_L} = \frac{2(\omega M V_{DD}/\pi)^2 R_L}{(R_t(R_r + R_L) + (\omega M)^2)^2}. \quad (26)$$

Differentiating (26) with respect to $R_L$ gives the load resistance that maximizes the load power, as follows:

$$R_{Lopt} = R_r + \frac{(\omega M)^2}{R_t}. \quad (27)$$

Substituting (27) into (26) yields:

$$P_{Lopt} = 0.5 \frac{(V_{DD}/\pi)^2 (\omega M)^2 / R_t}{R_t R_r + (\omega M)^2}. \quad (28)$$

Rearranging (28) with respect to the driver voltage gives:

$$V_{DD} = \frac{\pi}{\omega M} \sqrt{2 P_{Lopt} R_t (R_t R_r + (\omega M)^2)}. \quad (29)$$

The input power is:

$$P_t = \frac{V_{DD}}{2\pi} \int_0^{\pi/\omega} i_t(t) dt = 2 \left(\frac{V_{DD}}{\pi}\right)^2 \frac{R_r + R_L}{R_t(R_r + R_L) + (\omega M)^2}, \quad (30)$$

while its optimal value considering (27) is:

$$P_{topt} = \left(\frac{V_{DD}}{\pi}\right)^2 \frac{2R_r + (\omega M)^2/R_t}{R_t R_r + (\omega M)^2}. \quad (31)$$

Dividing (29) by (31) gives the efficiency of the wireless power transmission corresponding to the optimum load resistance:

$$\eta_{opt} = \frac{P_{Lopt}}{P_{topt}} = 0.5 \frac{1}{1 + \frac{2R_r R_t}{(\omega M)^2}}. \quad (32)$$

The general expression for the efficiency is:

$$\eta = \frac{P_L}{P_t} = \frac{(\omega M)^2}{R_t(R_r + R_L) + (\omega M)^2} \cdot \frac{R_L}{R_r + R_L}. \quad (33)$$

Differentiating (33) with respect to $R_L$ gives the load resistance that maximizes the efficiency:

$$R_{L\eta max} = \sqrt{R_r^2 + \frac{(\omega M)^2 R_r}{R_t}}. \quad (34)$$

The maximum efficiency can be calculated by substituting (34) into (33).

$$\eta_{max} = 0.5 \frac{1}{1 + \frac{2R_r R_t}{(\omega M)^2}}. \qquad (32)$$

The maximum efficiency and maximum load power for the parallel-loaded receiver is identical to that of the series one. The optimal load resistance and maximizing the efficiency for the parallel-loaded receiver differ from (27) and (34). However, the derivation is similar. The specific formulae for the load resistance is not developed here and instead we find the optimal resistance using computer simulations tool like PSPICE® (Cadence Design Systems, San Jose, Calif.), a full-featured, native analog and mixed-signal circuit simulation tool.

Figure 13:
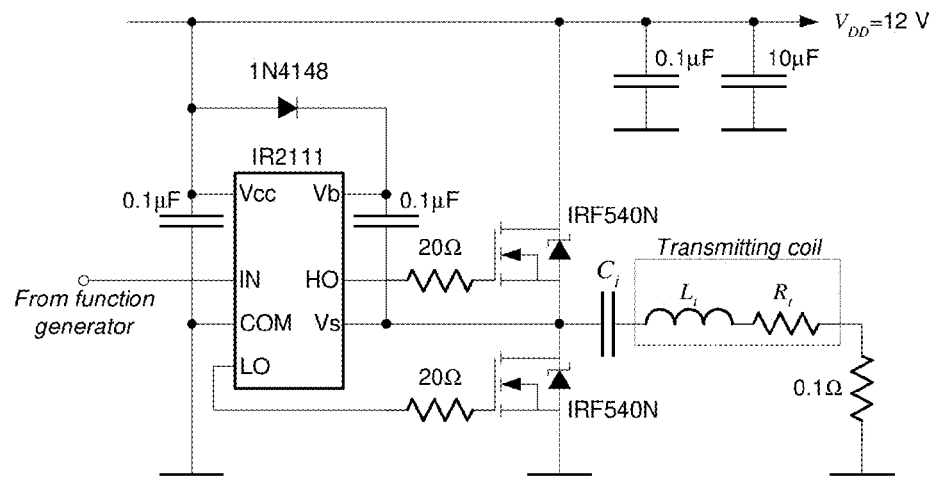
FIG. 13 shows a schematic of a transmitter circuit.

The circuit shown in FIG. 13 is a transmitter. The source Vdr is built from two BUZ11 N-MOSFETs driven by the IR2111 gate driver. The 0.1 Ohm resistor is used for the transmitter current monitoring. Both the transmitter and receiver capacitors are chosen with low ESR. The load resistance is chosen as $R_L$=0.5 Ohm, and the driver voltage $V_{DD}$=12 V. Substituting these values and the other setup parameters ($R_t$=1 Ohm, $R_r$=0.65 Ohm, M=2.056 pH) into (26) gives for $P_L$=3.16 W. The measured voltage amplitude on the load resistance is 1.75 V, which corresponds to $P_L$=3.1 W. The input power drawn from the power supply is $P_{in}$=$V_{DD}$/π·I=12/3.14·2.8=10.7 W. The efficiency is η=$P_L$/$P_{in}$=28%. It is noted that the load resistance is not optimized for the maximum output power.

Figure 14:
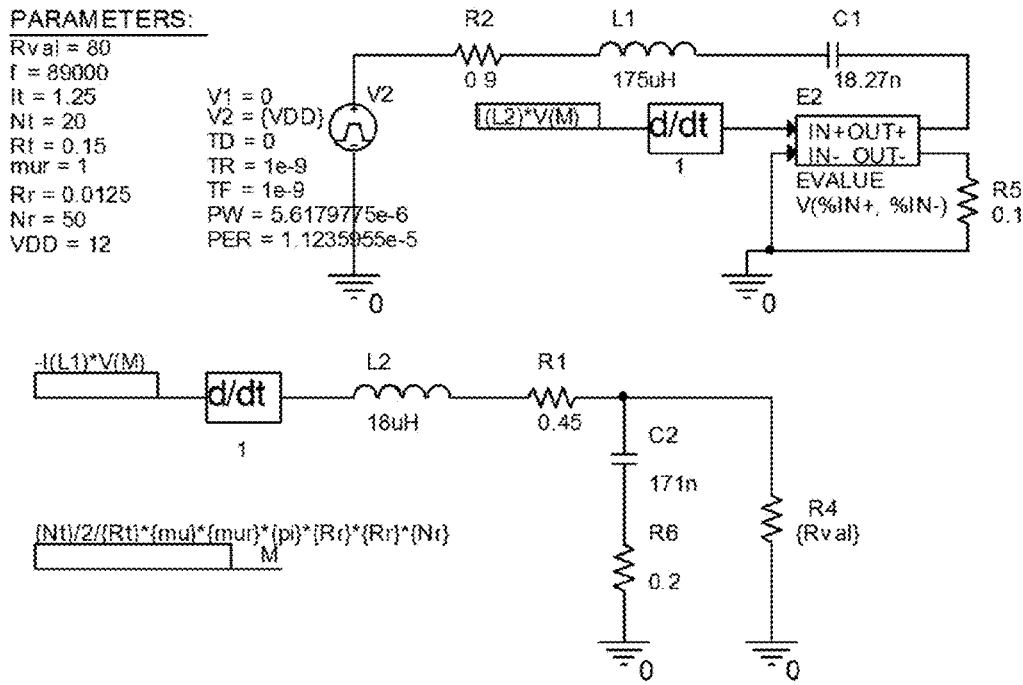
FIG. 14 shows a schematic of a parallel-loaded receiver circuit.

The circuit shown in FIG. 14 is a parallel-loaded receiver. The source V2 is built from two BUZ11 N-MOSFETs driven by the IR2111 gate driver. The 0.1 Ohm resistor is used for the current monitoring. Both the transmitter and receiver capacitors are chosen with low ESR. Substituting the model parameters into (29) gives $V_{DD}$=11.5 V for $P_L$=5 W. Computer simulations have shown that the maximum load power of 4.85 W is obtained for $R_L$=80 Ohm. This result closely correlates with laboratory measurements, where an output power of 4.5 W was measured for $V_{DD}$=12 V. The input power drawn from the power supply is $P_{in}$=$V_{DD}$/π·I=12/3.14·4.2=16.05 W. The efficiency is η=$P_f$/$P_{in}$=28%.

Figure 15:
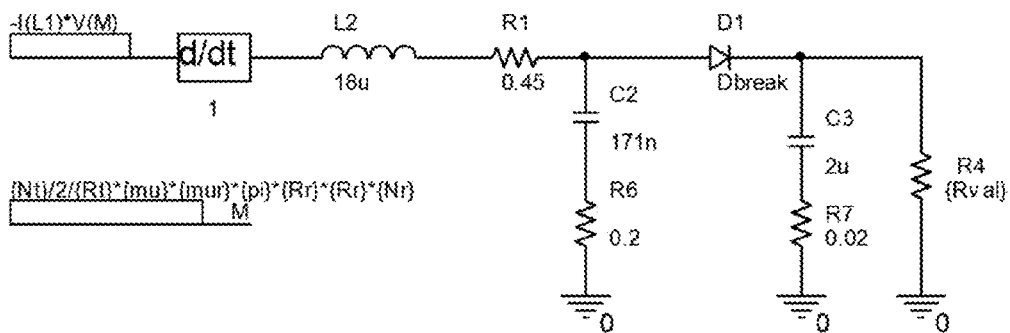
FIG. 15 shows a schematic whereby a simple single-phase rectifying circuit is added to a receiver.

Inserting a simple single-phase rectifying circuit before R4, as shown in the circuit in FIG. 15, takes about 0.2 W dissipated on the diode with 2 A peak diode current and 44 V peak diode reverse voltage. The peak voltage on the receiver capacitor is 25 V, and the peak voltage on the transmitter capacitor is 500 V.

Optimizing the Design of the Resonance Structure of the Transmitter and Receiver Several design factors contribute to the quality of the transmitter and receiver resonance structures of CET systems of the invention. Particularly, the resonance structure (e.g. resonance structure 202 as shown for the Receiver in FIG. 4) can be designed to minimize loss during the energy transfer. The quality of the resonance structure is dependent on the ratio between the inductance (L) to the resistance (R) of the coil. In radio frequency (RF) couplings, the quality of the resonance LC structure is dependent on the ratio of the inductance and capacitance (LC) to the resistance (R) of the coil. Those ratios are referred to herein as the quality factor (Q). Resonance LC structures are depicted in FIGS. 7 and 8. A higher Q indicates a lower rate of energy loss relative to the stored energy of the resonance structure. The quality factor (Q) of the coil originates in the coil's ohmic resistance, which can be calculated knowing the material and thickness of the coil, the diameter of the coil, D, the number of turns of coil, N, and the magnetic effects—the skin effect and the proximity effect (described below). In addition to the regular resistance and loss factors, a design may also take into consideration the skin effect and the proximity effect and the capacitor internal resistance.

The quality factor Q of the receiver and/or transmitter resonance structures can vary to provide optimum energy transfer. In certain embodiments, the quality factor of the transmitter is within the range of about 100 to about 500, and the quality factor of the receiver is within the range of about 50 to about 200.

In certain embodiments, the quality factor of the coils is improved with nongalvanic connected coils.

The following describes the various parameters that influence the Q of RF couplings.

The first parameter is a capacitor's or capacitors' equivalence series resistance (ESR) of the resonance structure of either the transmitter or receiver coils. For optimal Q, a capacitor's or capacitors' ESR in a resonance structure is less than the coil's active resistance. In certain embodiments, the capacitor's or capacitors' ESR is less than 5 times the coil's active resistance.

Another parameter that influences Q is the skin effect. The skin effect is the tendency of an alternating electric current (AC) to become distributed within a conductor such that the current density is largest near the surface of the conductor, and decreases with greater depths in the conductor. That is, the electric current flows mainly at the "skin" of the conductor, between the outer surface and a level called the skin depth. The skin effect causes the effective resistance of the conductor to increase at higher frequencies where the skin depth is smaller, thus reducing the effective cross-section of the conductor.

In order to reduce the skin effect in transmitter and receiver coils, the coils can be constructed using wires configured to transmit alternating currents, such as litz wire. A litz wire is a type of cable used in electronics to carry alternating current, and are made according to the "litz wire standards." Litz wires consist of many thin wire strands, individually insulated and twisted or woven together, following one of several known patterns often involving several levels (groups of twisted wires are twisted together, etc.). Litz wires suitable for use in systems of the invention include those manufactured by New England Wire Technologies (Libson, N.H.). Litz wire standards relate the number of internal strands to the wire structure. Litz wire sizes are often expressed in abbreviated format: N/XX, where N equals the number of strands and XX is the gauge of each strand in AWG (American Wire Gauge). Wires suitable for use in the invention have a gauge of 36-48 AWG (with the preferred gauge being 38-40 AWG). In certain embodiments, the external coil is a wire with 100-600 strands with a gauge of 36-48 AWG; and the internal coil is a wire with 100-400 strands with a gauge of 36-48 AWG. In preferred embodiments, the internal coil and the external coil are formed from a wire with 175 strands/40 AWG.

Another parameter that influences Q is the proximity effect. Proximity effect is the tendency for current to flow in loops or concentrated distributions due to the presence of magnetic fields generated by nearby conductors. The proximity effect is most evident in a conductor carrying alternating current, if currents are flowing through one or more other nearby conductors, such as within a closely wound coil of wire, the distribution of current within the first conductor will be constrained (or crowded into) to smaller regions. This current crowding is known as the proximity effect. This crowding gives an increase in the effective resistance of the circuit. The resistance due to the proximity effect increases with frequency. The proximity effect, in transmission and receiver coils relates to H1, H2 and coil center to center distance z (see FIG. 25). In the end, the proximity effect cannot be uncoupled from geometry, and must be calculated for a given design.

The following are additional optimization features that can also be incorporated into the transmitter and receiver of the CET systems of the invention.

Figure 23:
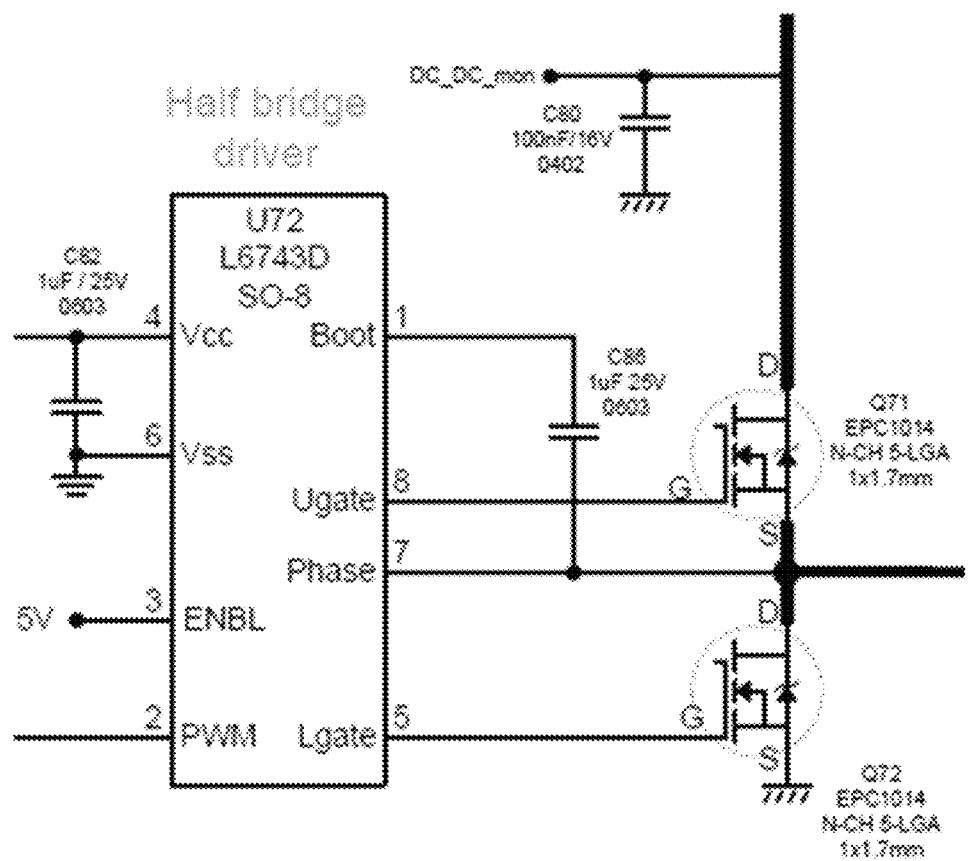
FIG. 23 depicts a preferred circuit for the half bridge Pulse generator.

In certain embodiments, the transmitter is optimized by incorporating a square generator, such as a half bridge pulse generator. The half-bridge pulse generator assists with pushing power from the transmitter to the receiver. FIG. 23 depicts a preferred circuit for to half bridge pulse generator. While the circuit depicted in FIG. 23 is a square wave generator, the circuit can generate regular sinusoidal waves in the transmitter coils.

Another optimization feature includes the incorporation of a field-effect transistor in the receiver and/or transmitter. A field-effect transistor (FET) is a transistor that uses an electric field to control the shape and hence the conductivity of a channel of one type of charge carrier in a semiconductor material. Particularly, FETs with low resistance when in saturation can greatly reduce losses due to heating.

Figure 24:
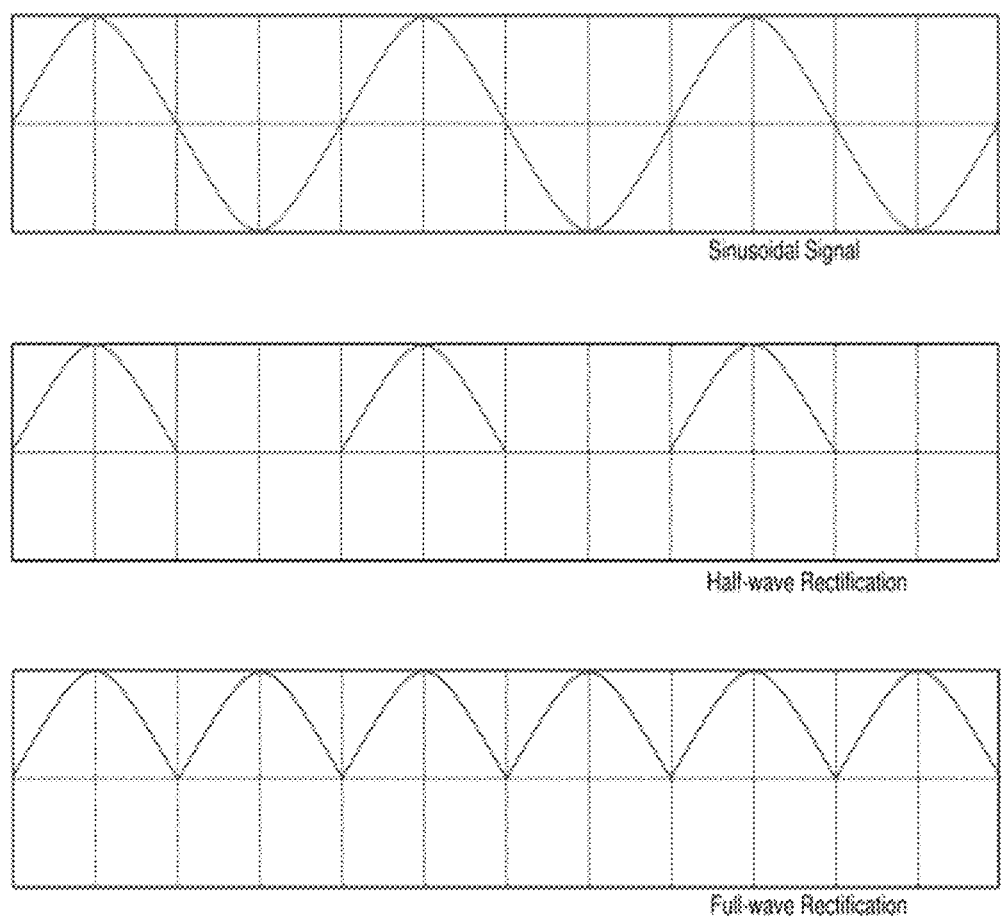
FIG. 24 illustrates rectification with one diode (half wave) and with a diode bridge (full wave).

In addition, an AC-to-DC conversion circuit may be included in the receiver in order to convert the AC voltage from an AC power source to DC voltage. The AC-to-DC conversion is a process known as rectification. In some embodiments, diodes can be utilized in systems of the invention to reduce loses in the AC to DC conversion circuit. Regular AC to DC conversions involve diode-based rectification circuits. Any rectifier may be used to convert AC voltage to DC current. In certain embodiments, CET systems may utilize a single diode rectification circuit or a diode bridge rectification circuit with the receiver. FIG. 24 illustrates rectification with one diode (half wave) and with a diode bridge (full wave). A diode bridge is an arrangement of four (or more) diodes in a bridge circuit configuration that provides the same polarity of output for either polarity of input. The advantage of the diode bridge is that it uses the entire input wave rather than only half of it.

According to some embodiments, the receiver includes a single diode rectifier. The effect of the single diode will be the same as using a diode bridge because the energy of the closed cycle of the single diode is not lost. Instead, the energy is kept the resonance structure for the active cycle. By using a single diode, only part of the duty cycle is used, and the potential difference in the resonance circuit will be significantly higher than built-in voltage drop across the diodes (around 0.7 V for ordinary silicon p-n junction diodes and 0.3 V for Schottky diodes). Thus, a single diode is able to reduce the transaction. In addition, the ratio of the diode's built-in voltage drop to the total voltage will be better. Also, the efficiency of the diode is related to the diode's size. Therefore, a system utilizing one diode in a rectifier of a certain size is more efficient than four diodes of the same size. In certain embodiments, the diode is a Schottky diode. Schottky diodes minimize the transition cycle loss.

Effect of a Coplanar Wireless Energy Transfer System's Design and Geometry on Power Transmission The geometry of the CET systems can affect the efficiency and robustness of the system. Accordingly, the geometry of certain systems can be optimized in accordance with the medical device being powered by a CET system. For example, the type of medical device, its power needs, and the implantation site are inputs that can be used to shape the geometry of a system for optimal energy transfer.

The following are key parameters that effect geometry and design of a CET system of the invention for use with an implant, such as a ventricular assist device (VAD). These systems include generally transmission of power from a belt or a vest transmitter that circumscribes the body in the same plane of the receiver. Optimal key parameters are suggested for and based on a typical VAD having a power requirement of 5 W-20 W and a peak of 30 W. In addition, the optimal key parameters for transmitters and receivers for use with a typical VAD are described in further detail separately below.

Figure 25:
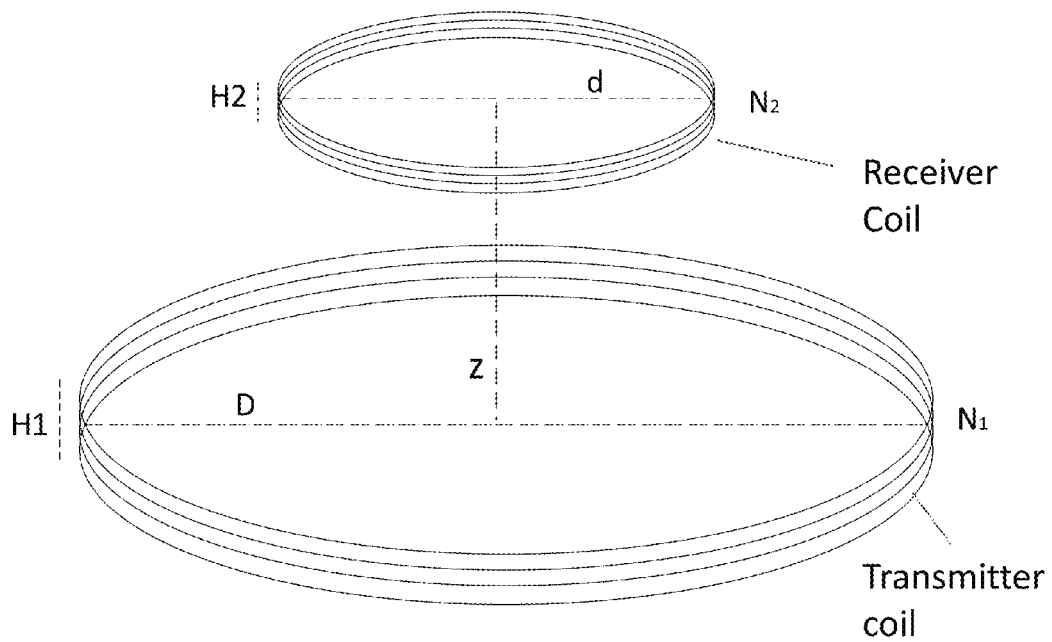
FIG. 25 illustrates the geometry of the transmitter coil and receiver coil and their relation to each other.

FIG. 25 depicts a layout of a CET system for use with a VAD. This layout is helpful for understanding geometry dependent factors. The distance Z, as shown in FIG. 25, is the distance between the centers of the transmitter and receiver coils. In general, the smaller the distance Z is, the better the coupling between the transmitter and the receiver. Preferably, the distance Z is 7 cm or less. Ideally, the receiver coils are concentric with the transmitter coils such that the distance Z is minimized. However, systems described herein maintain power transfer efficiency while allowing distance Z of about 7 cm between the centers of the transmitter and the receiver.

In addition, the diameters of transmitter and receiver coils (see FIG. 25) effect power transmission in a system. Diameter D is the diameter of the external transmitter, which depends and can be adjusted based on the body size of a patient. Diameter d is diameter of the internal receiver. The diameter d of the internal transmitter can be varied depending on the type and placement of the device. As diameter d increases, so does the quality of the coupling between the transmitter and receiver. The ratio of the receiver diameter d to the transmitter diameter D also affects wireless power transmission. In general, a higher diameter ratio increases the quality of the coupling for energy transfer.

Further, the number of wire turns of the transmitter coil N1 and receiver coil N2 also influences power transmission. The greater number of turns of wire in either coil improves magnetic/electronic conversion. However, the resistance caused by the number of wire turns should also be taken into consideration.

Other design considerations that influence power transmission are the capacitor's ESR and the type of wire used (both of which were discussed in further detail above). For optimization, the capacitor's ESR should be as low as practical, and a litz wire should be used to minimize skin effect.

A. Transmitter Geometry and Design

The following are preferable design and geometry details of the transmitter.

According to certain embodiments, the diameter of the transmitter coil D, as shown in FIG. 25, can be sized to fit around an individual's body. In certain embodiments, the diameter D ranges from, for example, about 20 cm (for children) to about 60 cm (overweight adult).

In certain embodiments, the transmit frequency may be in the range of about 60 KHz to about 1 MHz. As discussed in more detail above, the CET system can be designed to search across a range of frequencies such that the transmitter couples to the resonance frequency of the receiver. This search may be automatic. For automatic frequency searches, the range of frequencies searched (e.g. a dynamic band of frequencies) are narrower than the range of the transmit frequency. In addition, a transmitter may be set at a target frequency or a resonance frequency. The dynamic band may be between 80 KHz and 300 KHz. In other embodiments, the dynamic band may be 80 KHz to 140 KHz. The target frequency may be a frequency within the range of 90 KHz to 115 KHz.

Figure 21:
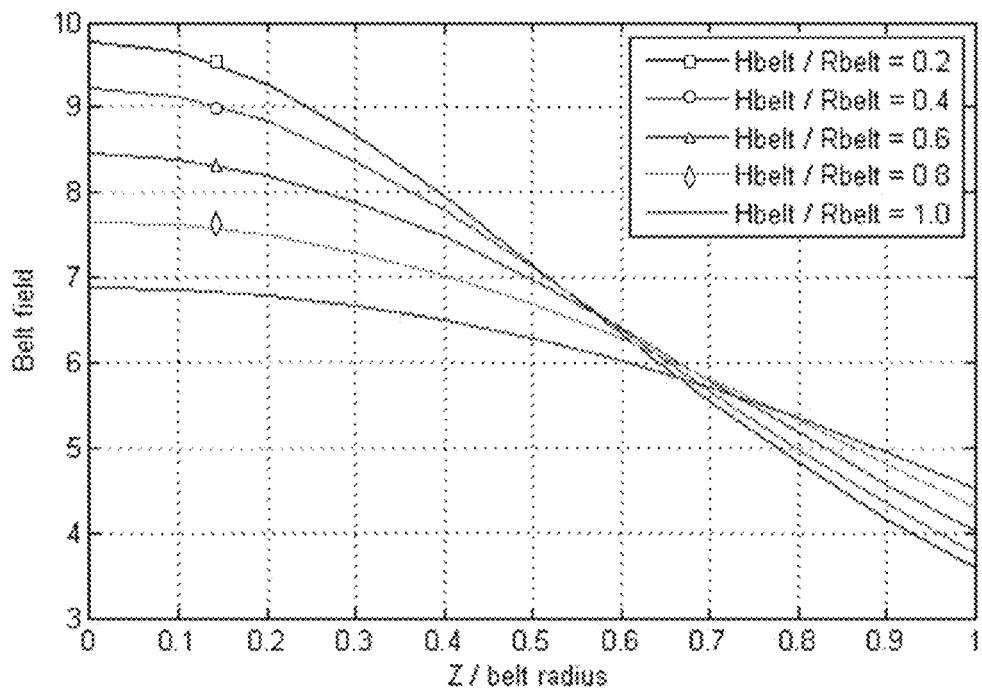
FIG. 21 illustrates the effect that the height of a transmitter coil has on robustness of power transfer if the proximity effects are ignored.
Figure 22:
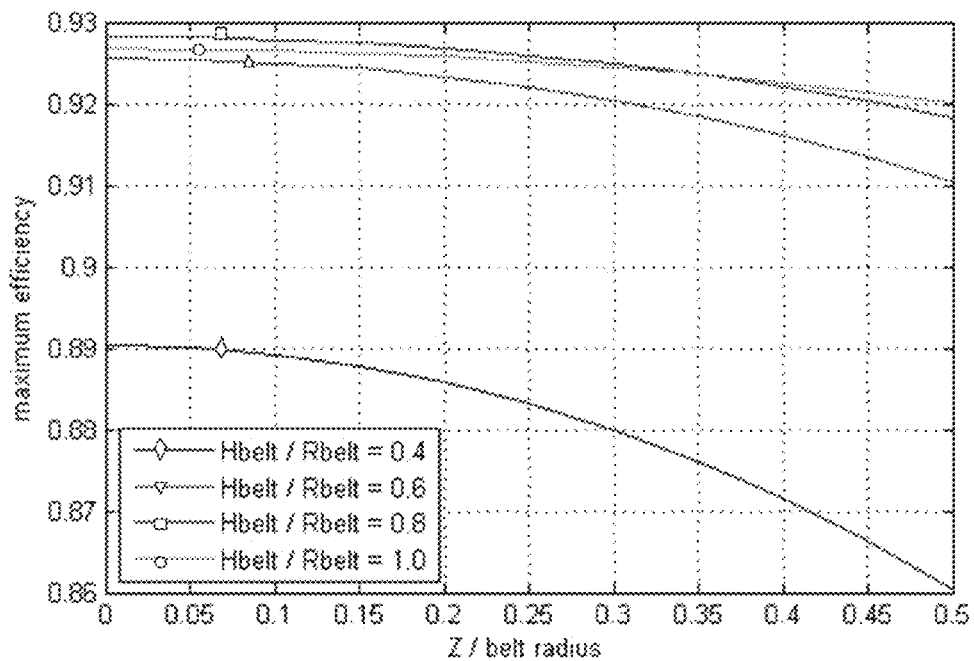
FIG. 22 illustrates the effect that the height of a transmitter coil has when the proximity effects are considered.

The height H1 of the transmitter coil can be designed to minimize proximity effect. Ideal heights H1 for minimizing proximity effects range from about 3 cm to 20 cm. FIG. 21 illustrates the effect that the height of a transmitter coil has on robustness of power transfer if the proximity effects are ignored. FIG. 22 illustrates the effect that the height of a transmitter coil has when the proximity effects are considered.

In certain embodiments, the height H1 is 0.4-1.5 times the size of the radius (the radius being half of the diameter D). That is, a ratio between the height H1 of the transmitter coil and the radius (D1/2) of the transmitter coil is 0.4-1.5. For example, if transmitter coil has a radius of 15 cm, the ideal height H1 ranges from 6-22.5 cm. In some embodiments, the ratio between the height H1 and the radius (D1/2) is about 0.6, 0.8, or 1. Preferably, the ratio is in the range of about 0.8-1. In certain embodiments, the height H1 for optimum efficiency is 12 cm.

According to certain embodiments, the transmitter diameter D is substantially larger than the distance Z between the center of the transmitter and receiver coils. This configuration reduces the effect of dynamic changes in distance Z during coplanar wireless energy transfer (e.g. due to movement of the transmitter compare to the receiver within the body). As a result, power transfer is more reliable and continuous despite the change in Z. The combination of a) transmitter diameter D larger than the distance Z with b) a height H1 to radius (D/2) ratio in the range of 0.8-1 further improves energy transfer.

Figure 26:
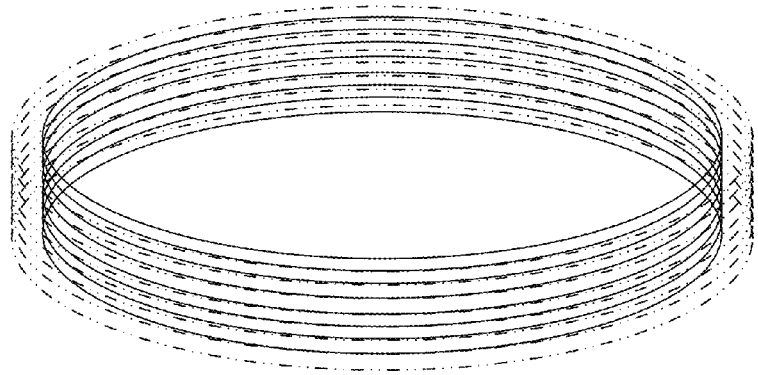
FIG. 26 depicts a transmitter coil having 16 wire turns arranged in two layers (e.g. 8 turns per layer).

The influence of the number of turns N1 on power transmission depends on the type of wire used and the quality factor of the coil. Using litz wires with 100-600 strands/36-48 AWG, the number of turns N1 of the transmitter coil may range from 6 to 35, preferably 20. In addition, the number of turns N1 may be arranged in 1-3 layers. FIG. 26 depicts a transmitter coil having 16 wire turns arranged in two layers (e.g. 8 turns per layer).

In certain embodiments, a capacitor of the transmitter should have an ESR that is less 5× the coil's active resistance and preferably 1/10 of the Coils resistance. Preferred wires for the transmitter are litz wires with 100-600 strands/ 36-48 AWG.

B. Receiver Geometry and Design

The following are preferable design and geometry details of the receiver.

According to certain embodiments, the diameter d of the receiver coil, as shown in FIG. 25, can be sized to fit to an anatomic location within the patient. For a receiver coil located in the pericardium, the diameter d may range from, for example, about 7 cm (children pericardium) to about 20 cm (adult pericardium and one plural cavity).

The ideal number of turns N2 of the receiver coil may range from 5 turns to 50 turns. The turns may be arranged in one to three layers (similar to the transmitter coil depicted in FIG. 26). Preferably, the receiver coil includes 20 turns in one layer.

Like the transmitter coil, the receiver coil can be designed to overcome the proximity effect. There are two different receiver coil designs that can be used to overcome the proximity effect. These designs can also be applied to the transmitter coil. The first design is a connected ring coil and the second design is a separated ring coil. Both designs may include a covering around the inductive wires. The covering is preferably biocompatible and provides insulation. Suitable materials include polymers, such as silicone (e.g. NiSil Med 4735 or Med 421), or epoxy materials. Ideally, the receiver coil is able to collect power for the implant, while maintaining enough flexibility to rest within the diaphragm area.

A connected ring coil design is one in which the coil's wire loops or turns are united such that the distance (i.e. pitch) between each turn is substantially constant. In certain embodiments, a single covering layer connects the coil's turns into a single connected structure. Connected ring coils have some flexibility, but the basic structure of the ring coil is maintained with enough rigidity to ensure that the distance (i.e. pitch) between each turn is substantially constant. Having a uniform minimum distance is best for reducing proximity effect. Pitch is the distance between the center of one turn and the next. The structure of the connected ring coil avoids/minimizes proximity effect of electromagnetism. The flexibility of the connected ring coil can be altered to suit, for example, its intended implantation area. The flexibility depends on the materials chosen for the wire and covering—varying based on those materials' parameters for elongation, tensile, durometer, hardness. In one embodiment, the structure of the connected ring coil has a height of about 1 cm to about 3 cm and a pitch of about at least 0.1 inch. In other embodiments, the pitch is at least 0.5 inches. In some embodiments, the pitch between turns is chosen to be substantially equal to the diameter of wire, which acts to further minimize proximity effect. Connected ring coils of the invention ideally have a narrow, small range of resonance frequency, making it easier to gauge and adapt to the resonance frequency. This narrow resonance frequency characteristic simplifies the calibration and control of the system.

A separated ring coil design includes turns (i.e. rings) that are separated to allow variable pitch and other movement between the turns. This provides more flexibility to the receiver geometry. In order to allow variable pitch and other movement, the turns of the coil are not fully connected to each other such that the rings can move away from each other to a desired extent. For example, only a portion of the turns is coupled so there is more movement between the rings. In other words, a separated ring coil is a coil that has one or more connecting points between turns (or rings), which act to provide flexibility in one or more directions, while preventing over-expansion and over-compression. The movement can be in the pitch direction (e.g. movement between turns) or can be in the lateral direction (upward or downward movement of side by side turns). The flexibility of the separated ring coil can be altered to suit, for example, its intended implantation area. The flexibility depends on the materials chosen for the wire and covering varying based on those materials' parameters for elongation, tensile, durometer, hardness.

Figure 27:
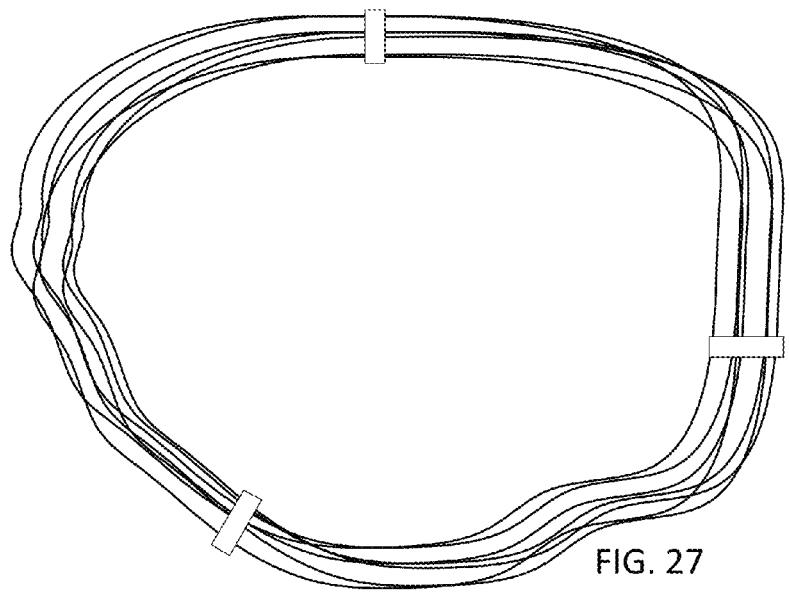
FIG. 27 depicts a separated ring coil according to certain embodiments.
Figure 28:
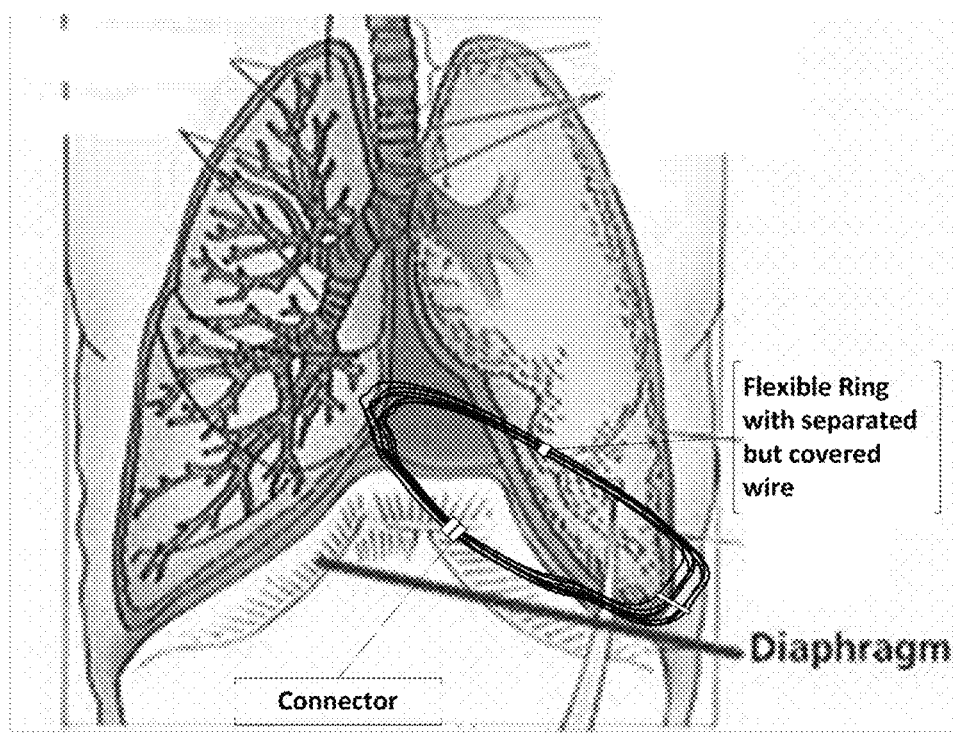
FIG. 28 depicts a separated ring coil disposed within a plural cavity and pericardium.

The separated ring coil may also have a covering for insulation, but the covering does not form a single connected structure. Instead, the covering may only partially connect the rings together at one or more points. In certain embodiments, the covering does not connect the rings together, but one or more separate connectors are placed on the coil to connect the rings together (such as the connectors shown in FIGS. 27 and 28). The benefit of the connectors is that a doctor can place them on or manipulate their positions on the ring coil during implantation of the transmitter within the body. This makes it easier to implant the transmitter within the body (such as in the pericardium, plural, or both). FIG. 28 depicts a separated ring coil disposed within a plural cavity and pericardium.

While the variable pitch and added movement of separated coils allows for easier implantation, the variable pitch may result in proximity effect if the wires are too close to each other. In order to prevent proximity effect, the invention provides for covering the wire of the separated ring coil with a covering material of a certain thickness to provide a minimal pitch distance between rings. For example, the covering of the ring coil may be 0.05 inch thick, such that the pitch between any two rings touching each other is at least 0.1 inches. The second receiver coil design for reducing pitch is use of separate but covered flexible wires for the receiver coil. In other embodiments, separated but covered wires are used for the receiver coil.

Various modifications may be made to the embodiments disclosed herein. The disclosed embodiments and details should not be construed as limiting but instead as illustrative of some embodiments and of the principles of the invention.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A system for wirelessly powering a ventricular assist device (VAD), comprising:
   a receiver inductive coil associated with the VAD and configured to be implanted within the pericardium of a patient to wirelessly receive inductively-transferred electromagnetic power from external to the patient and provide that received power to the VAD; and
   a transmitter inductive coil configured to be disposed externally around a body of the patient such that the transmitter inductive coil externally surrounds the patient's body and the implanted receiver inductive coil, the transmitter inductive coil also configured to inductively transfer the electromagnetic power into the body and to the receiver inductive coil, the transmitter inductive coil comprising a height and a radius, a ratio of the height to the radius being about 0.4 to about 1.5.

2. The system of claim 1, wherein the transmitter inductive coil, the receiver inductive coil, or both comprise a wire configured to carry alternating currents.

3. The system of claim 2, wherein the wire comprises 100 to 600 strands with a gauge ranging from 36 AWG to 38 AWG.

4. The system of claim 3, wherein the wire of the receiver inductive coil comprises 130 to 300 strands with a gauge ranging from 36 AWG to 38 AWG.

5. The system of claim 2, wherein the wire of the transmitter inductive coil comprises 175 to 400 strands with a gauge ranging from 36 AWG to 38 AWG.

6. The system of claim 1, wherein the transmitter inductive coil comprises 6 to 35 turns of a wire.

7. The system of claim 1, the receiver inductive coil comprises 5 to 50 turns of a wire with a pitch of at least 0.05 inches between each turn.

8. The system of claim 1, wherein the transmitter inductive coil is associated with a microprocessor, and the microprocessor searches for a resonance frequency of the receiver inductive coil within a frequency range and locks the resonance frequency of the transmitter inductive coil with the resonance frequency of the receiver inductive coil.

9. The system of claim 1, wherein the frequency range is from 300 KHz to 80 KHz.

10. The system of claim 1, wherein the transmitter inductive coil is associated with a capacitor that comprises an equivalent series resistance that is less than a resistance of the transmitter inductive coil.

11. The system of claim 1, wherein the transmitter inductive coil is configured to transmit the electromagnetic power at a frequency ranging from 60 KHz to 1 MHz.

12. The system of claim 1, wherein the transmitter inductive coil is associated with a half-bridge pulse generator.

13. The system of claim 1, wherein the receiver inductive coil is associated with an AC-to-DC rectification circuit that comprises a single diode.

14. The system of claim 2, wherein the receiver inductive coil comprising 5 to 50 turns of a wire with a pitch of at least 0.05 inches between each turn.

15. The system of claim 14, wherein each of the wire turns of the receiver inductive coil is connected such that the pitch is substantially constant.

16. The system of claim 14, wherein the wire turns of the receiver inductive coil are coupled such that the pitch is variable, and the receiver inductive coil comprises a covering such that the pitch between any two wire turns is 0.05 inches or more.

17. A receiver inductive coil associated with a medical device and configured to be placed in the pulmonary cage of a patient to wirelessly receive inductively-transferred electromagnetic power from external to the patient and provide that received power to the medical device, the receiver inductive coil comprising 5 to 50 turns of a wire with a pitch of at least 0.05 inches between each turn, the inductively-transferred electromagnetic power being transmitted by a transmitter inductive coil configured to be disposed externally around and surround the patient's pulmonary cage.

18. The receiver inductive coil of claim 17, wherein the wire is configured to carry alternating currents.

19. The receiver inductive coil of claim 18, wherein the wire comprises 100 to 600 strands with a gauge ranging from 36 AWG to 48 AWG.

20. The receiver inductive coil of claim 19, wherein the wire comprises 130 to 300 strands with a gauge ranging from 36 AWG to 48 AWG.

21. The receiver inductive coil of claim 20, wherein the wire comprises 175 strands with a gauge of 40 AWG.

22. The receiver inductive coil of claim 17, wherein the wire turns are arranged in 1 to 3 layers.

23. The receiver inductive coil of claim 17, wherein each of the wire turns of the receiver inductive coil is connected such that the pitch is substantially constant.

24. The receiver inductive coil of claim 17, wherein the wire turns of the receiver inductive coil are coupled such that the pitch is variable, and the receiver inductive coil comprises a covering such that the pitch between any two wire turns is 0.05 inches or more.

25. The receiver inductive coil of claim 17, wherein the receiver inductive coil is associated with an AC-to-DC rectification circuit that comprises a single diode.

26. The receiver inductive coil of claim 17 wherein the receiver inductive coil is configured to be disposed within a pleural cavity of the patient.

* * * * *